US009452279B2

(12) United States Patent
Stevens et al.

(10) Patent No.: US 9,452,279 B2
(45) Date of Patent: Sep. 27, 2016

(54) VARIABLE DISPLACEMENT INFLATION DEVICES AND METHODS OF USE

(71) Applicant: Merit Medical Systems, Inc., South Jordan, UT (US)

(72) Inventors: Brian Stevens, Pleasant Grove, UT (US); William Padilla, Sandy, UT (US); Steven Weir, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 404 days.

(21) Appl. No.: 14/021,054

(22) Filed: Sep. 9, 2013

(65) Prior Publication Data
US 2014/0088498 A1 Mar. 27, 2014

Related U.S. Application Data

(60) Provisional application No. 61/704,299, filed on Sep. 21, 2012.

(51) Int. Cl.
*A61M 5/178* (2006.01)
*A61M 25/10* (2013.01)

(52) U.S. Cl.
CPC .............. *A61M 25/10182* (2013.11); *A61M 2005/1787* (2013.01)

(58) Field of Classification Search
CPC ........................................... A61M 2005/1787
See application file for complete search history.

(56) References Cited

U.S. PATENT DOCUMENTS

| 1,234,582 | A | * | 7/1917 | Trueblood ................... 604/191 |
| 3,370,754 | A | * | 2/1968 | Cook et al. .................. 222/132 |
| 3,606,094 | A | | 9/1971 | Mills et al. |
| 4,476,866 | A | | 10/1984 | Chin |
| 4,702,737 | A | * | 10/1987 | Pizzino ........................ 604/191 |
| 4,758,223 | A | | 7/1988 | Rydell |
| 4,929,238 | A | | 5/1990 | Baum |
| 5,209,732 | A | | 5/1993 | Lampropoulos et al. |
| 5,306,248 | A | | 4/1994 | Barrington |
| 5,752,935 | A | | 5/1998 | Robinson et al. |
| 5,860,955 | A | | 1/1999 | Wright et al. |
| 6,793,660 | B2 | | 9/2004 | Kerr et al. |
| 7,717,880 | B2 | | 5/2010 | Denolly |
| 2004/0267308 | A1 | | 12/2004 | Bagaoisan |
| 2010/0185156 | A1 | | 7/2010 | Kanner et al. |

FOREIGN PATENT DOCUMENTS

| EP | 0565045 A1 | 10/1993 |
| WO | WO00/78386 | 12/2000 |
| WO | WO2012/094403 | 7/2012 |

OTHER PUBLICATIONS

International Preliminary Report dated Apr. 2, 2015 for PCT/US2013/060062.

(Continued)

*Primary Examiner* — F. Daniel Lopez
(74) *Attorney, Agent, or Firm* — Stoel Rives LLP

(57) ABSTRACT

An inflation device that may comprise multiple plungers is disclosed. The inflation device may have multiple configurations wherein certain plungers are locked with respect to a body of the inflation device while others are configured to be displaceable within the body. Each plunger may be configured with a different effective surface area, allowing a practitioner to vary the amount of force required to attain certain pressures.

21 Claims, 31 Drawing Sheets

(56) References Cited

OTHER PUBLICATIONS

International Preliminary Report dated Apr. 2, 2015 for PCT/US2013/060641.
Notice of Allowance dated Apr. 14, 2015 for U.S. Appl. No. 14/031,746.
Restriction Requirement dated Jun. 26, 2014 for U.S. Appl. No. 14/031,746.
Office Action dated Sep. 24, 2014 for U.S. Appl. No. 14/031,746.
International Search Report and Written Opinion dated Dec. 18, 2013 for PCT/US2013/060641.
International Search Report and Written Opinion dated Dec. 18, 2013 for PCT/US2013/060062.
International Preliminary Report on Patentability dated Mar. 24, 2015 for PCT/US2013/060062.
Notice of Allowance dated May 12, 2015 for U.S. Appl. No. 14/031,746.
Extended European Search Report dated Apr. 19, 2016 for EP13838878.0.
Extended European Search Report dated Apr. 19, 2016 for EP138391271.

* cited by examiner

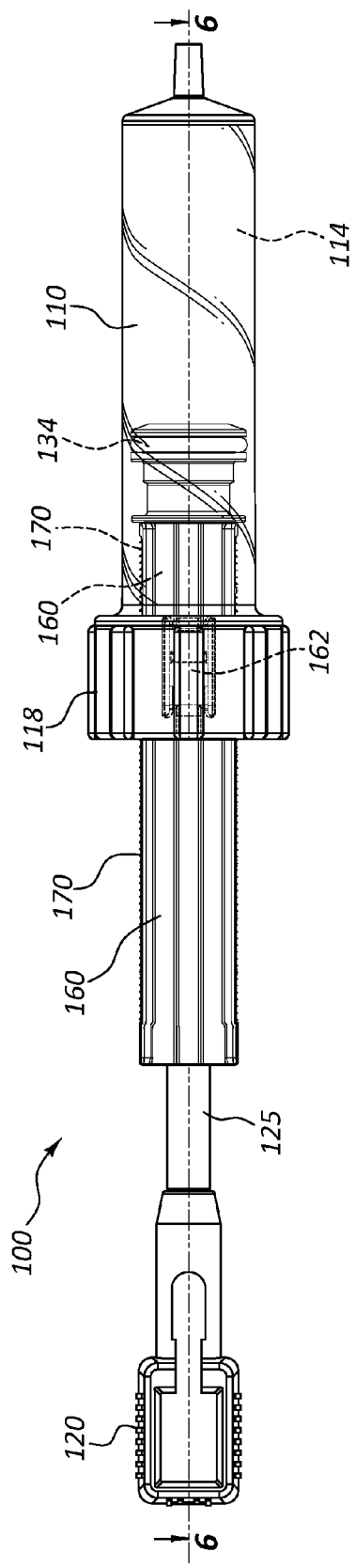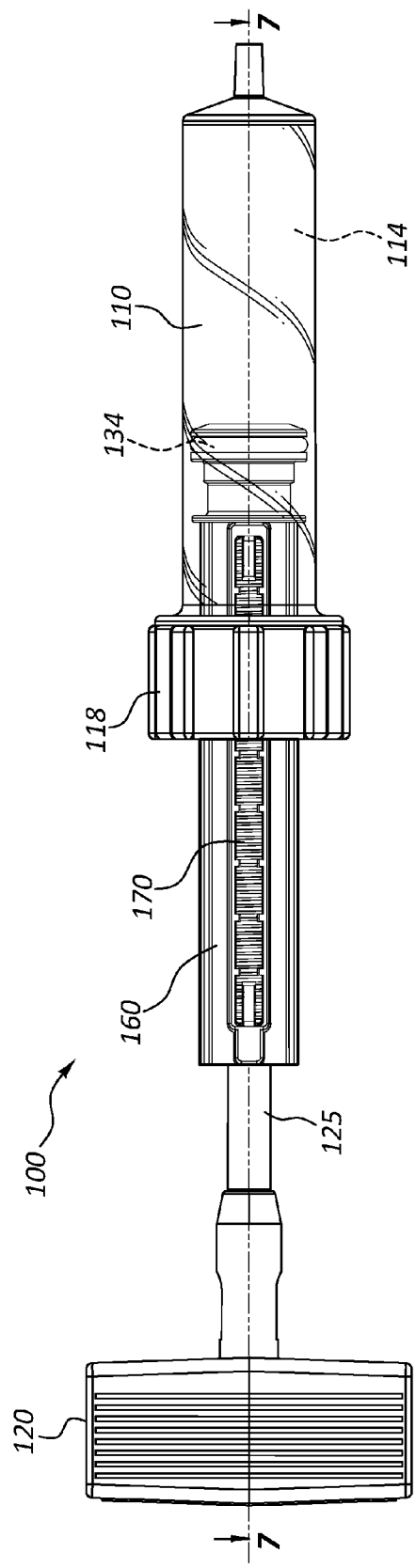
FIG. 4
FIG. 5

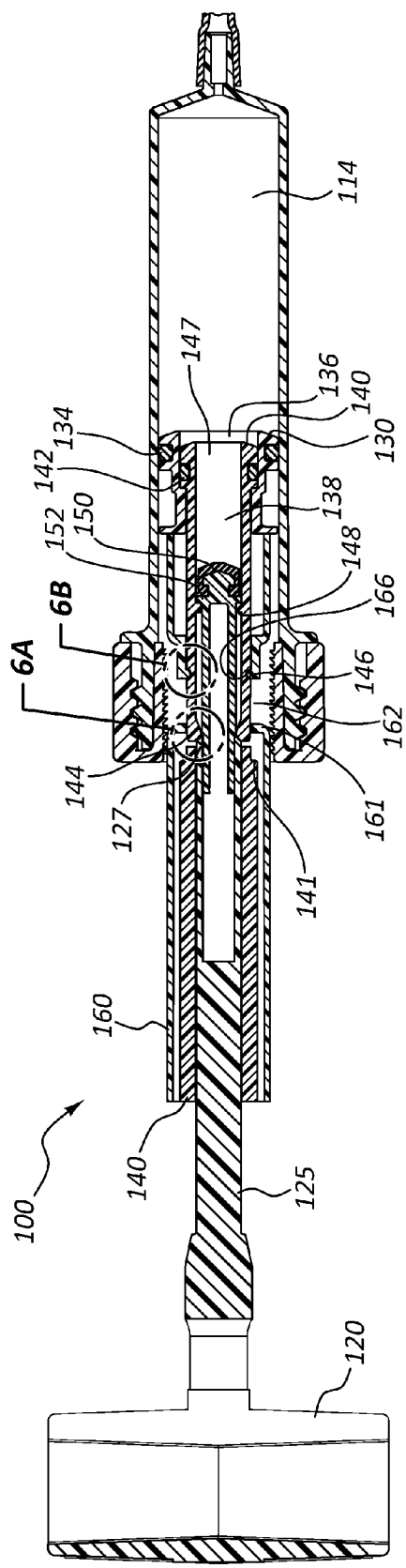
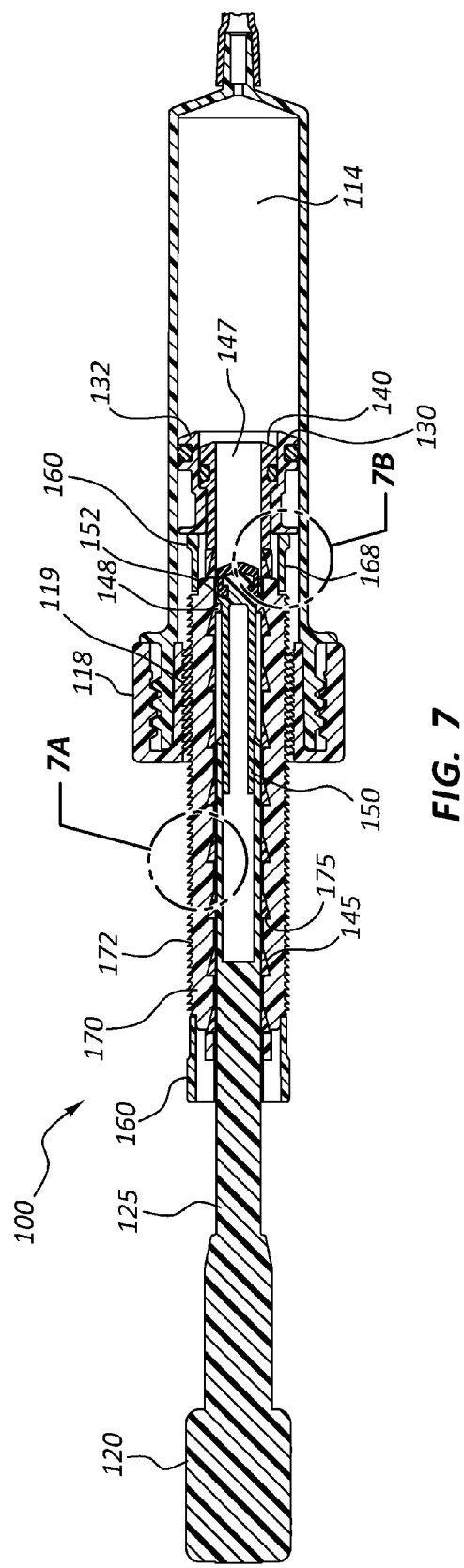
FIG. 6
FIG. 7

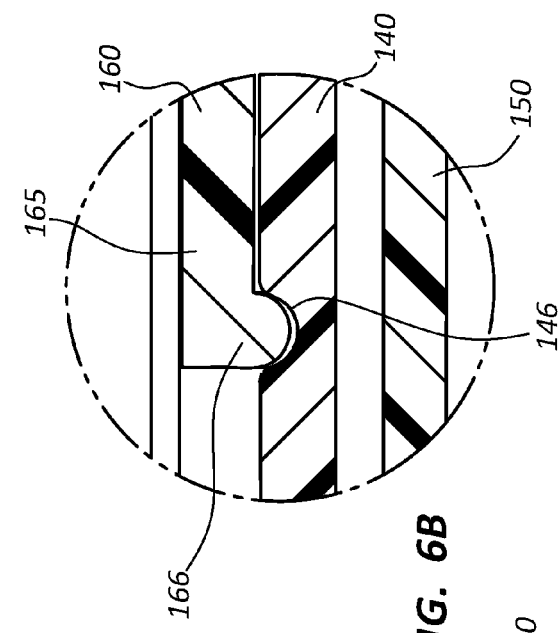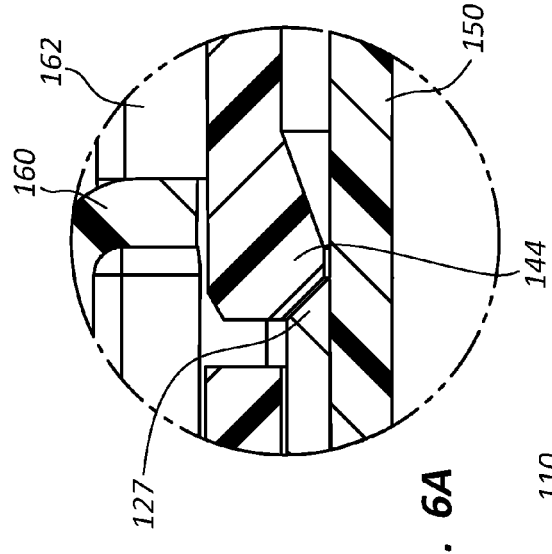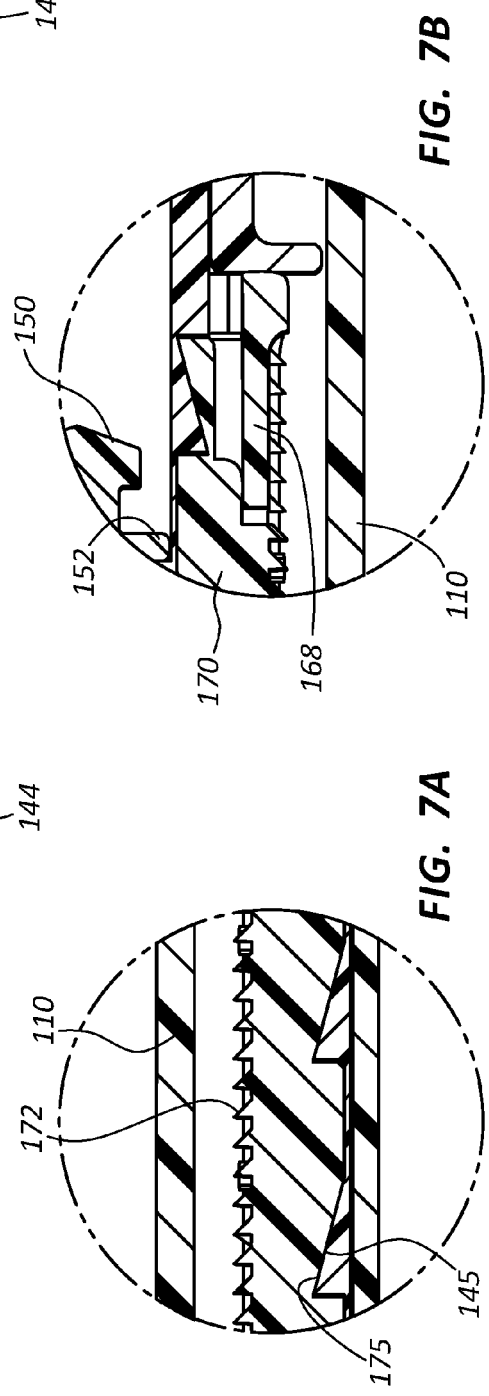

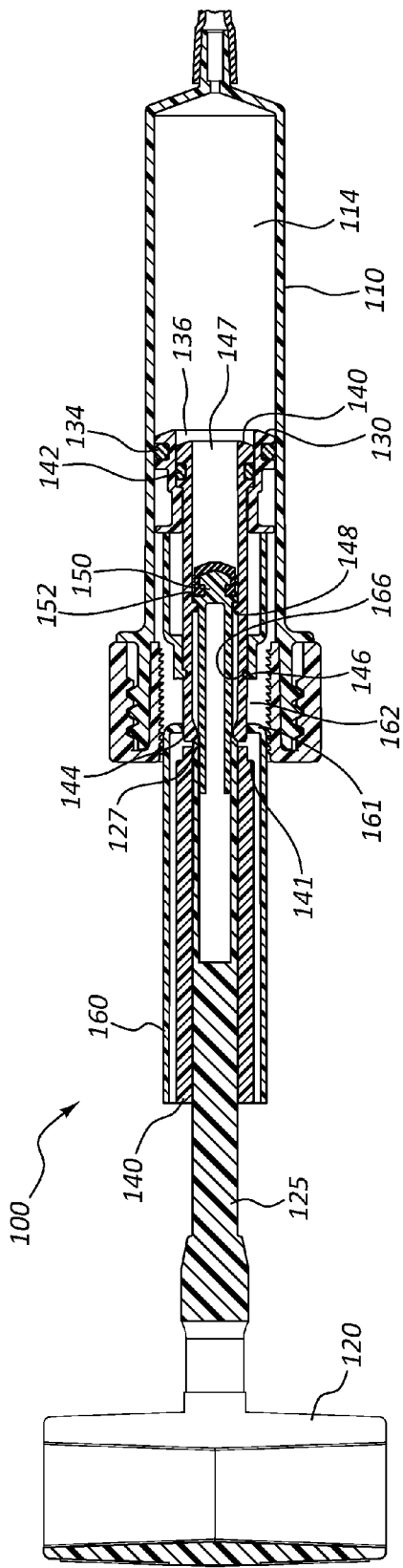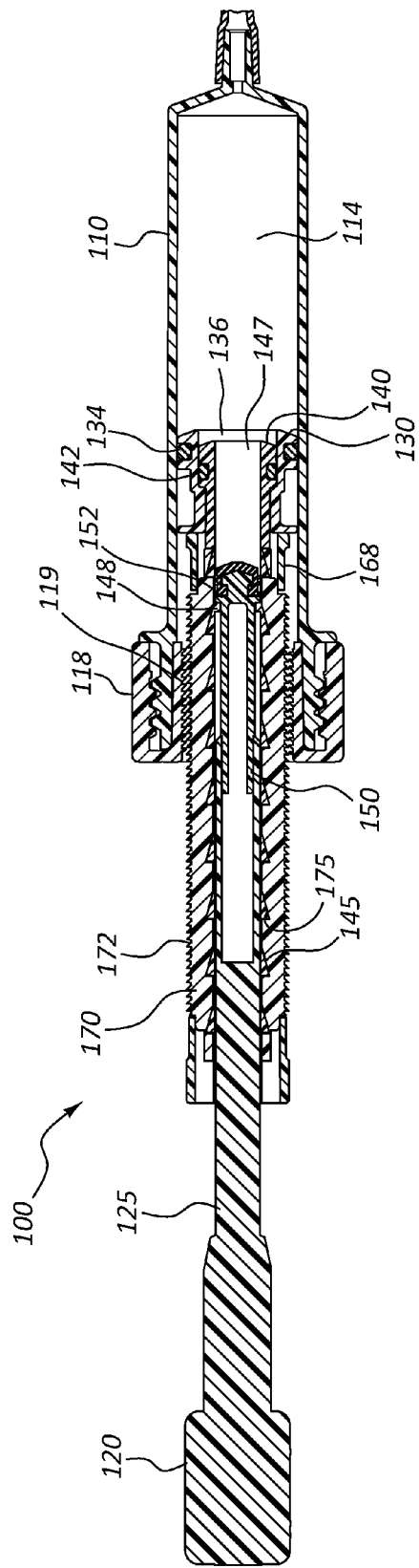
FIG. 8A
FIG. 8B

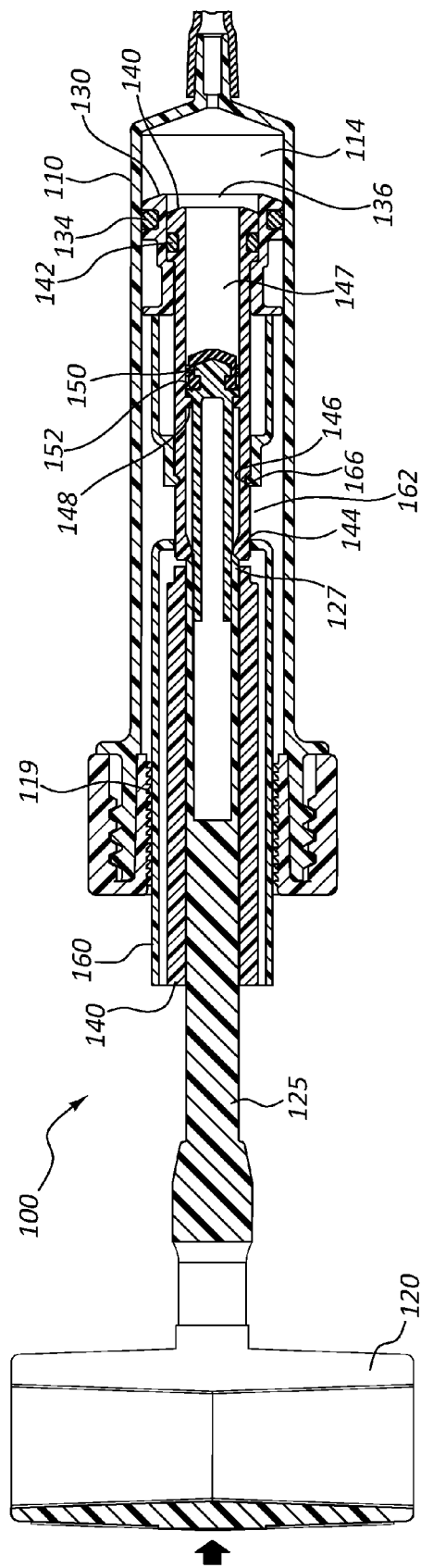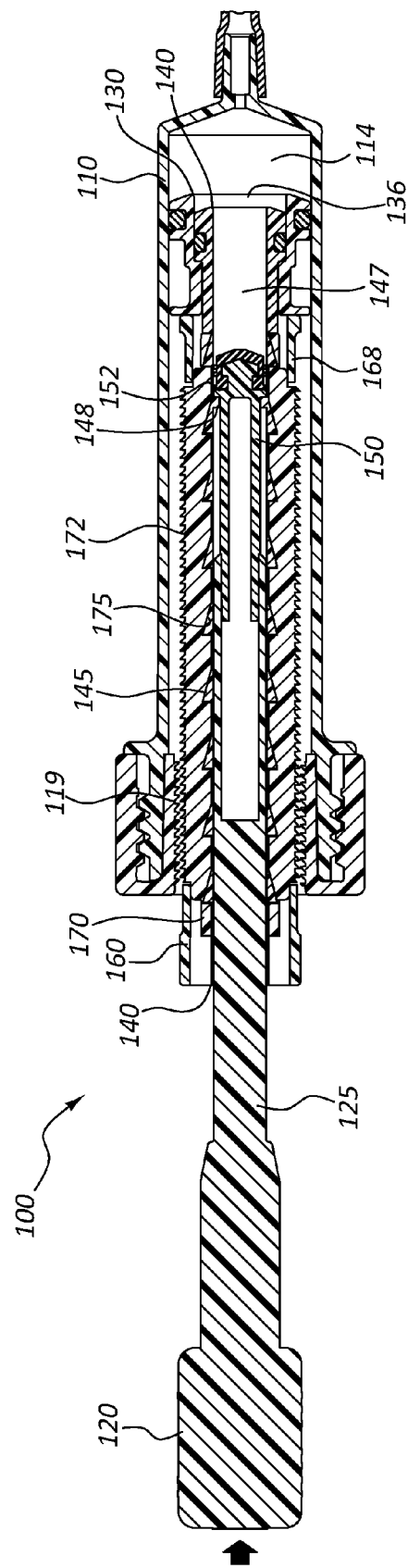

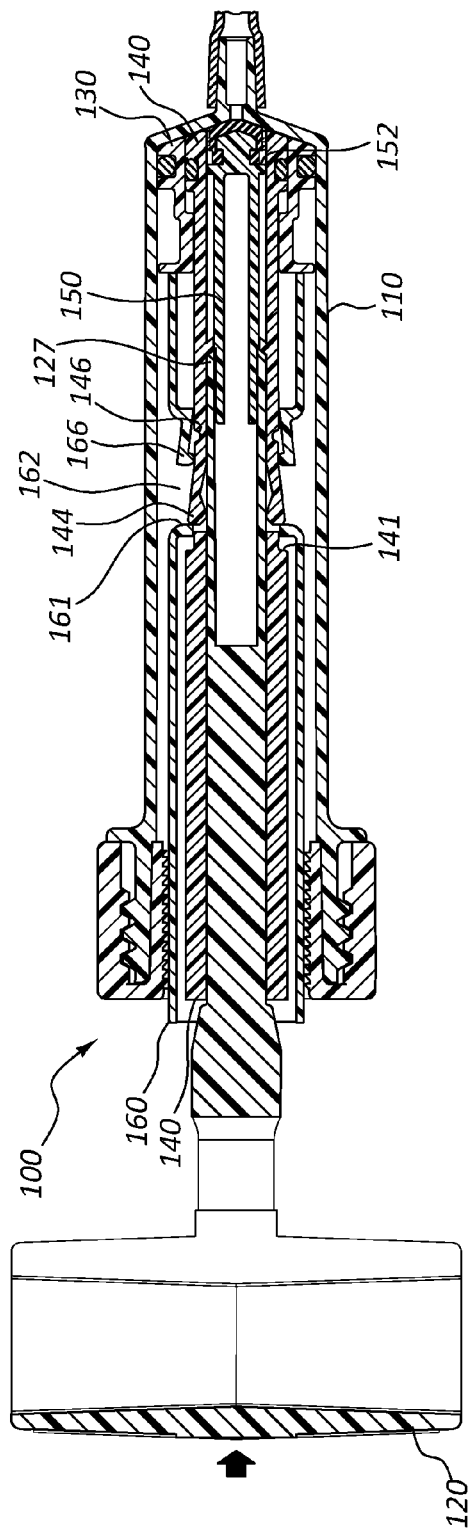
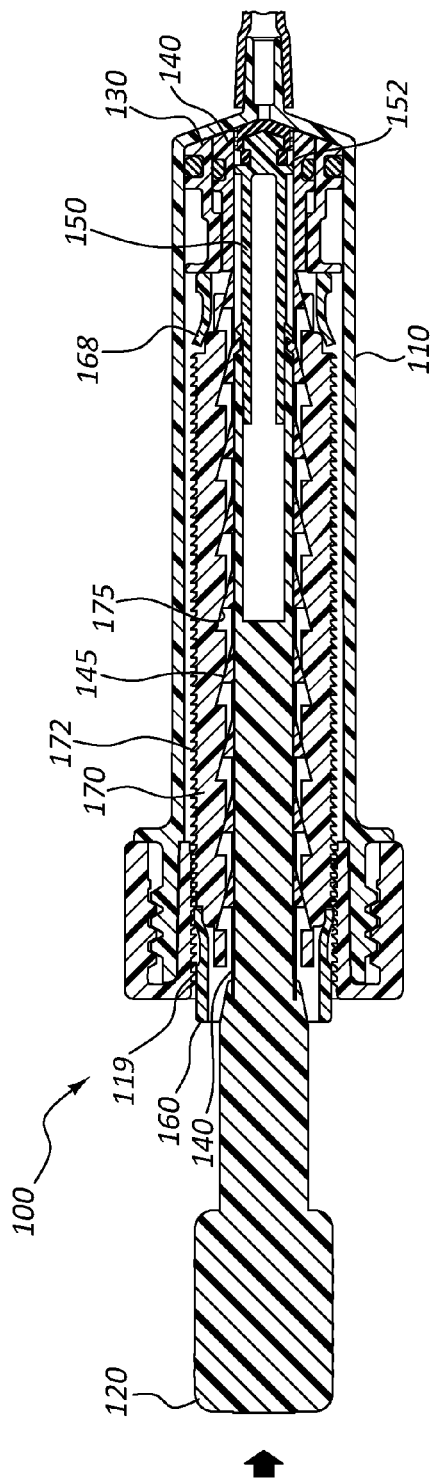
FIG. 11A
FIG. 11B

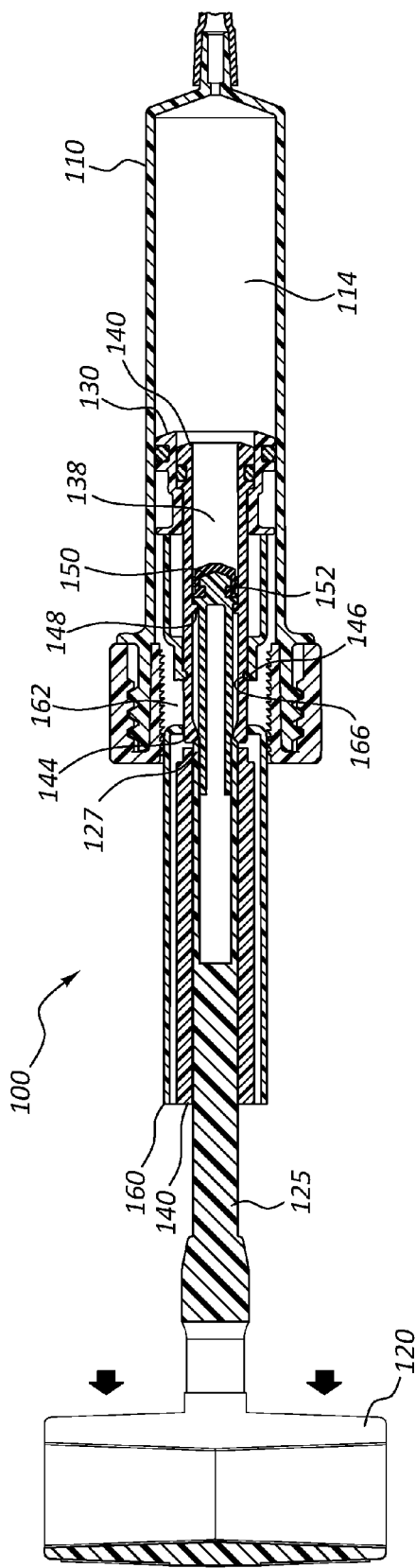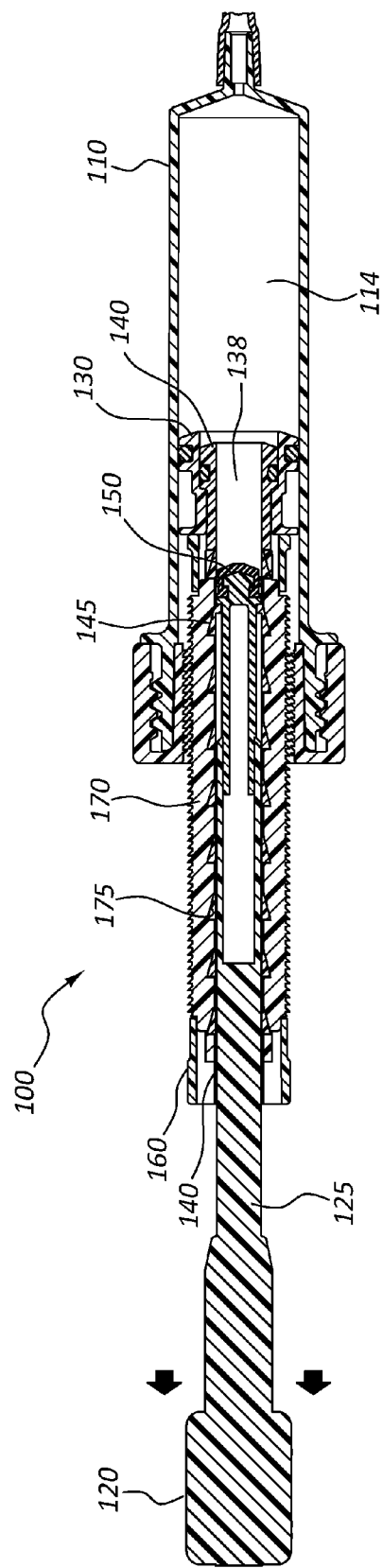
FIG. 12A
FIG. 12B

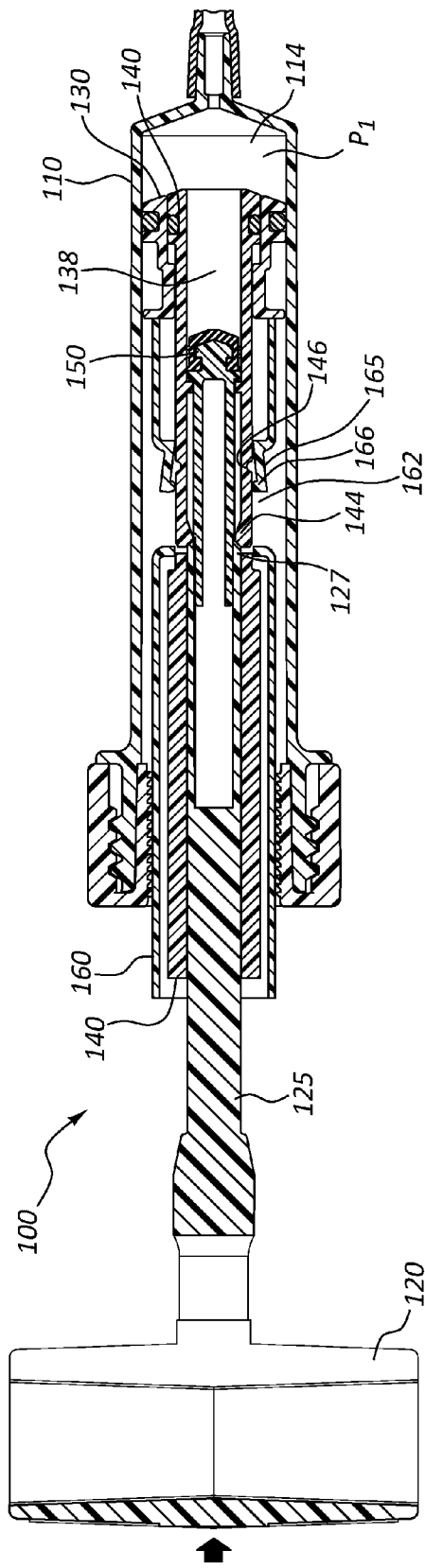
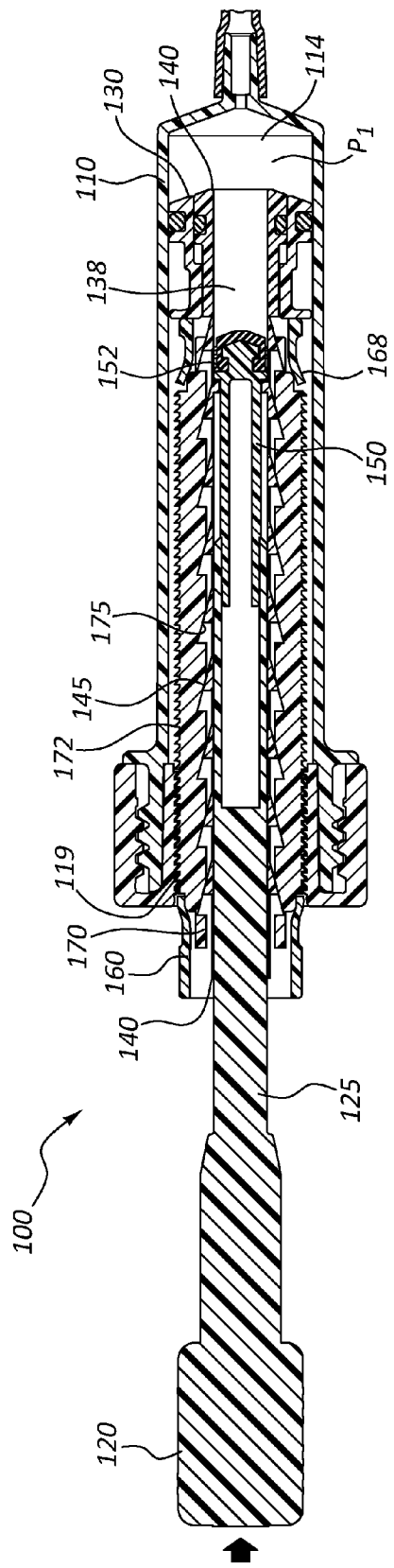
FIG. 13A
FIG. 13B

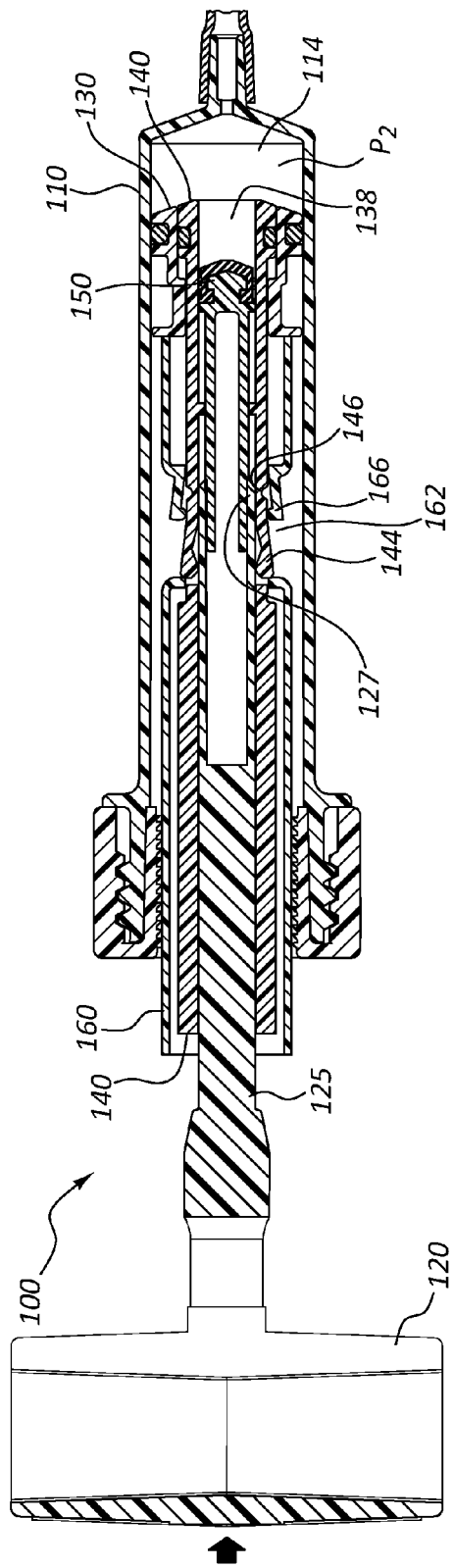
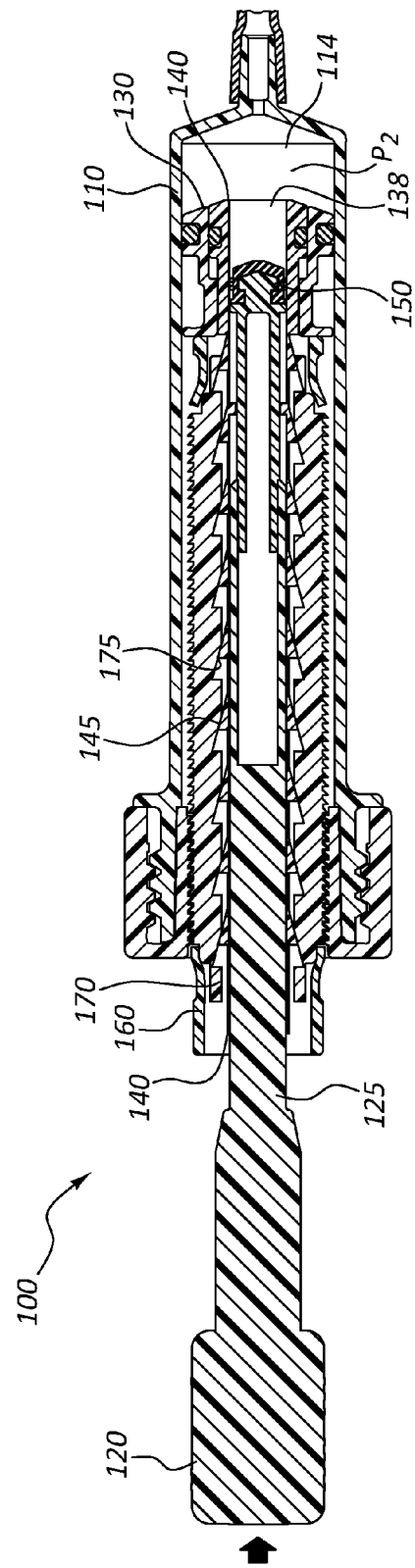
FIG. 14A
FIG. 14B

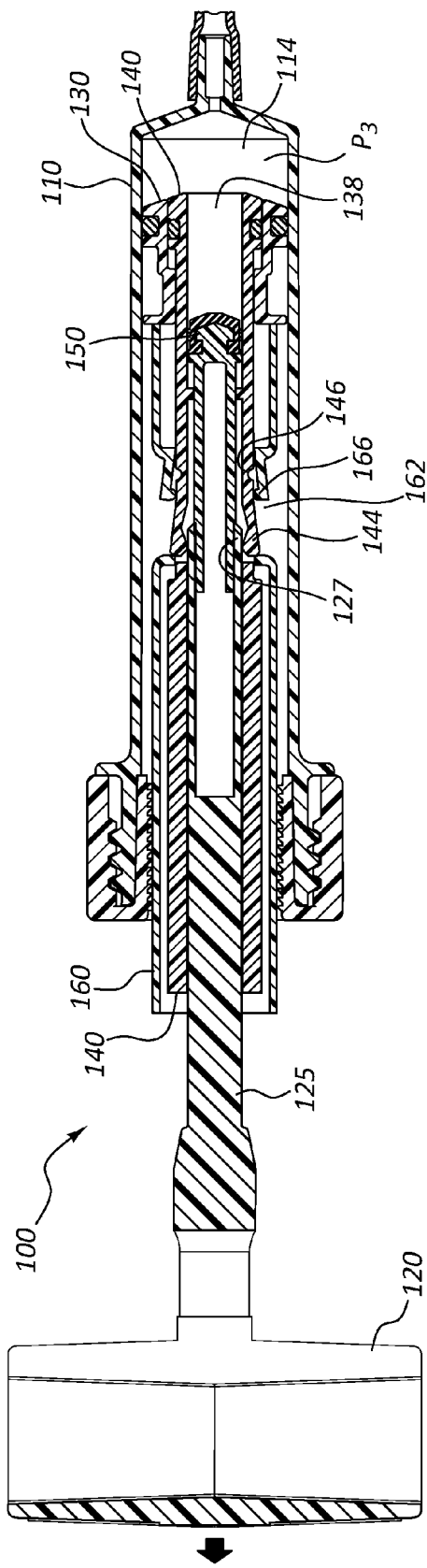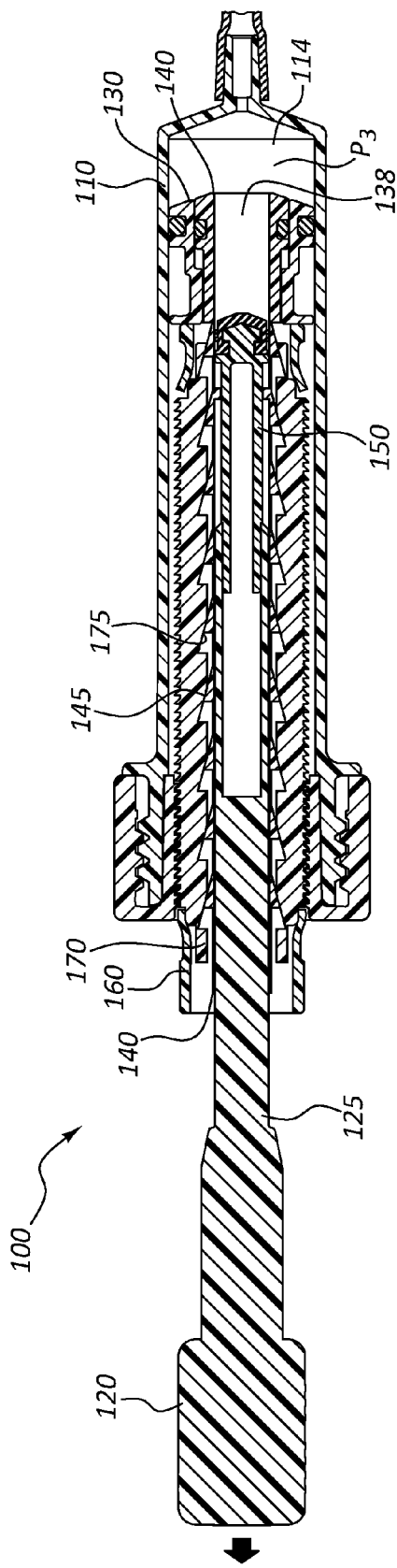
FIG. 15A
FIG. 15B

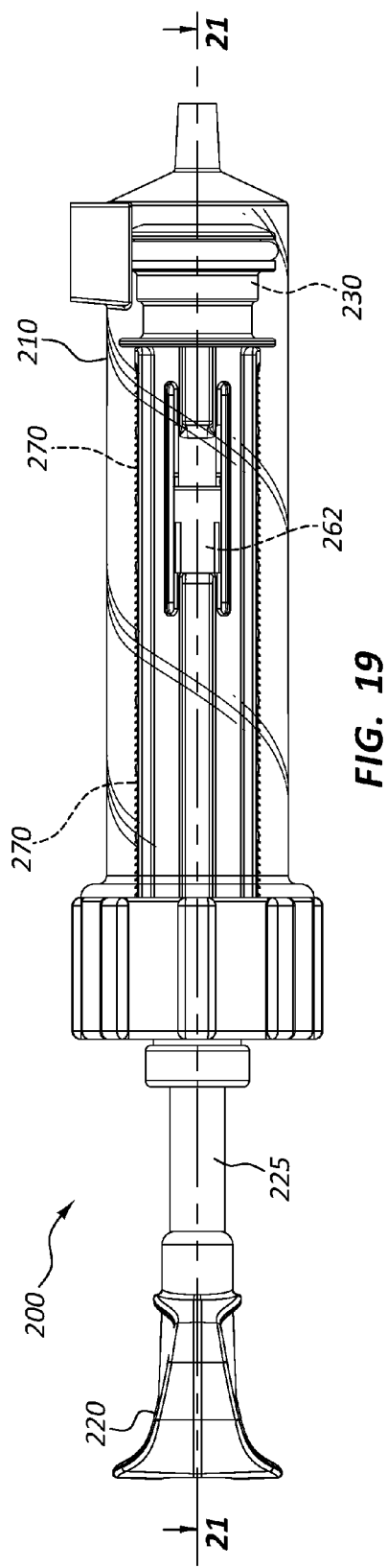
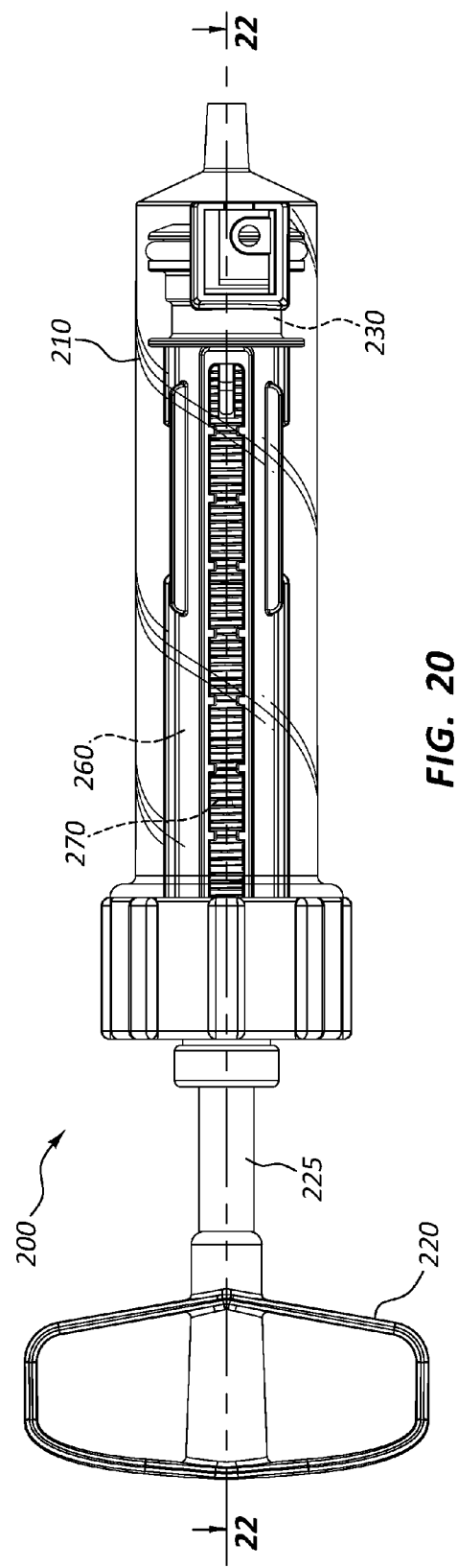
FIG. 19
FIG. 20

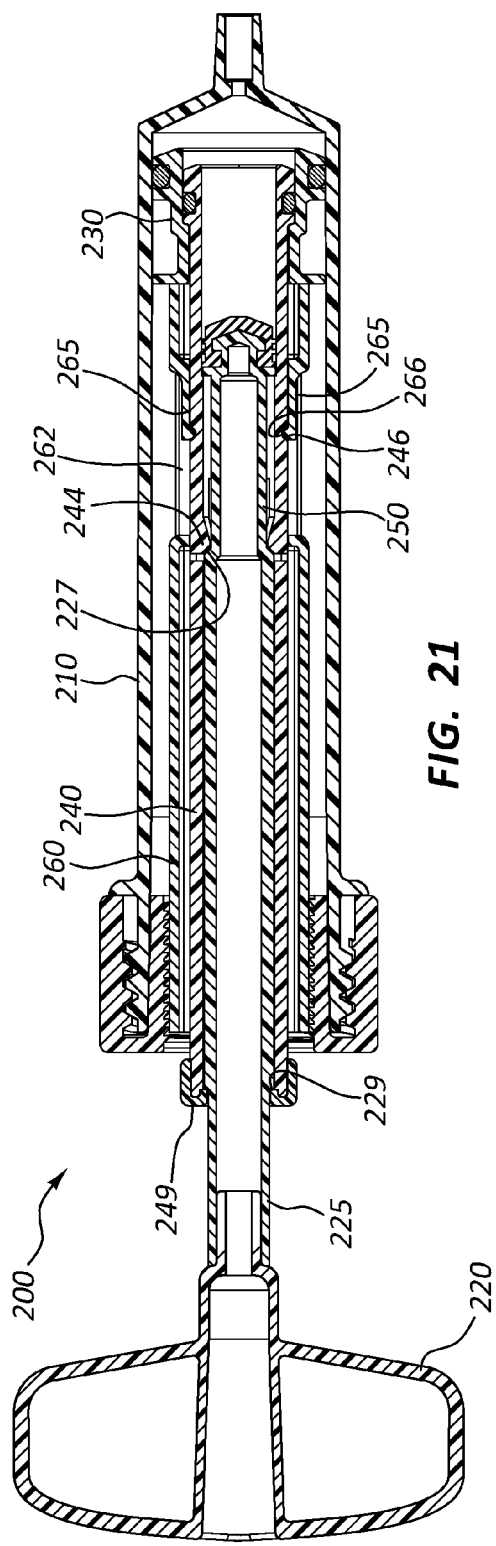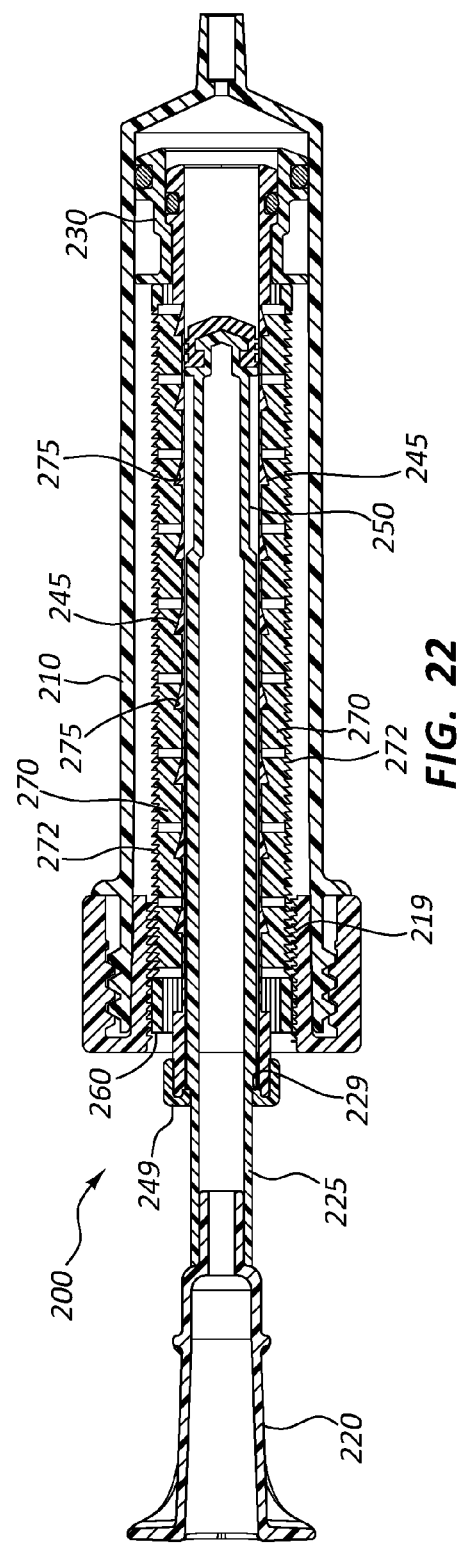

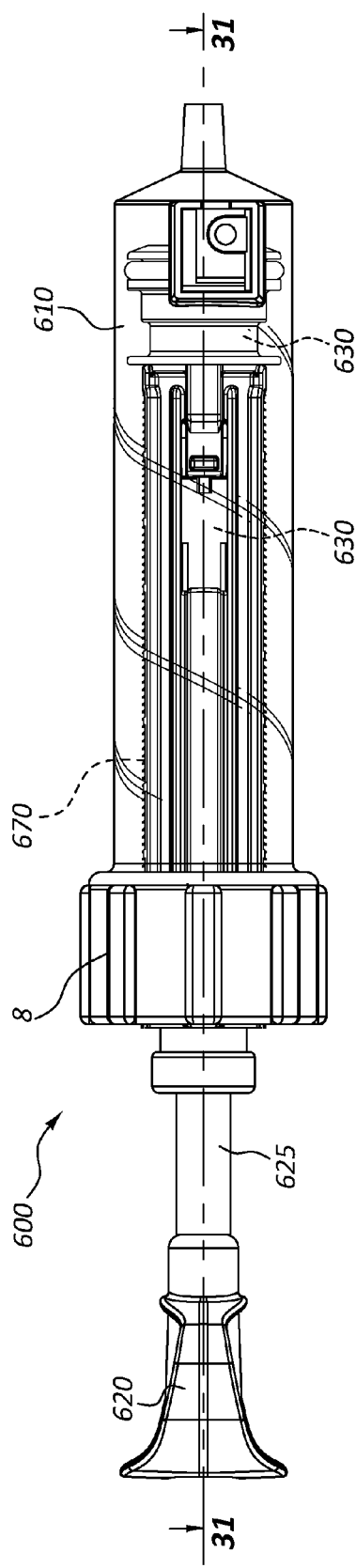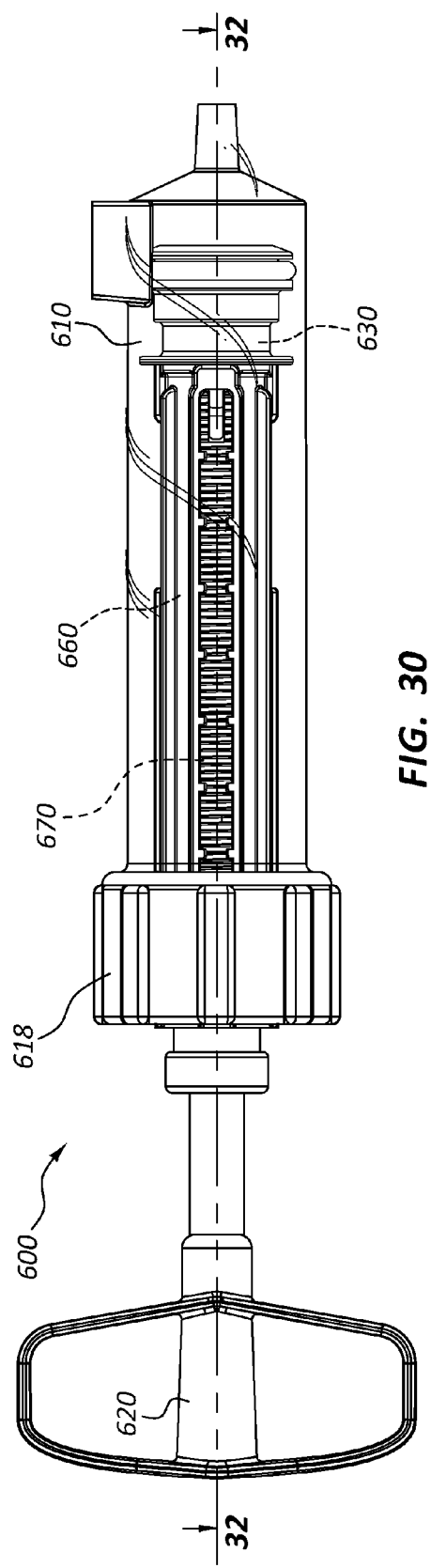
FIG. 29
FIG. 30

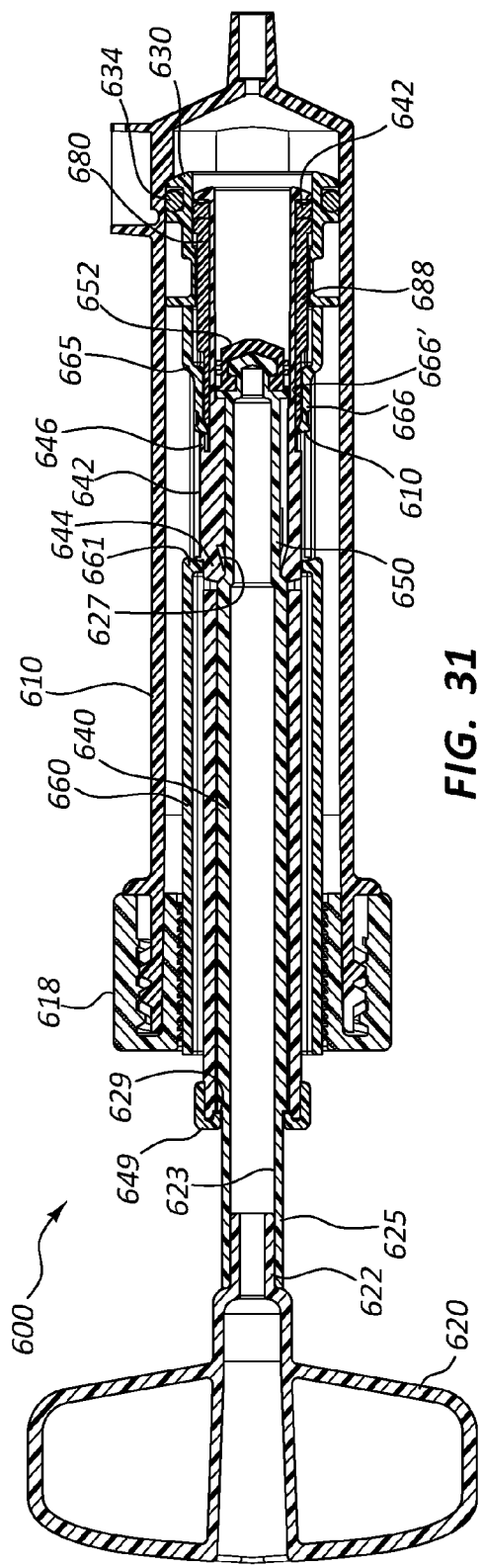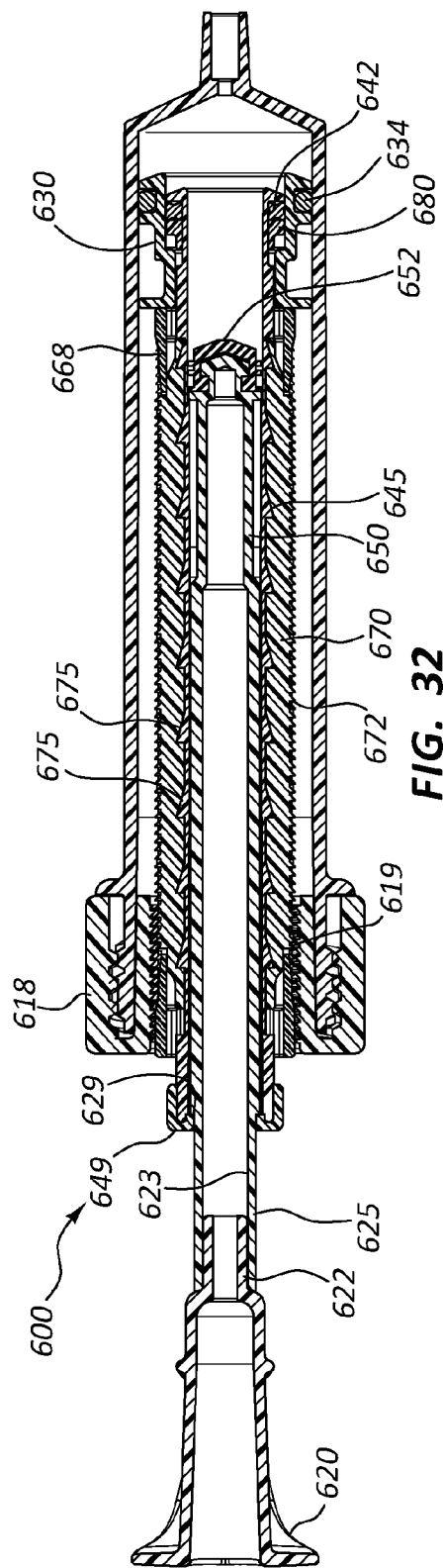

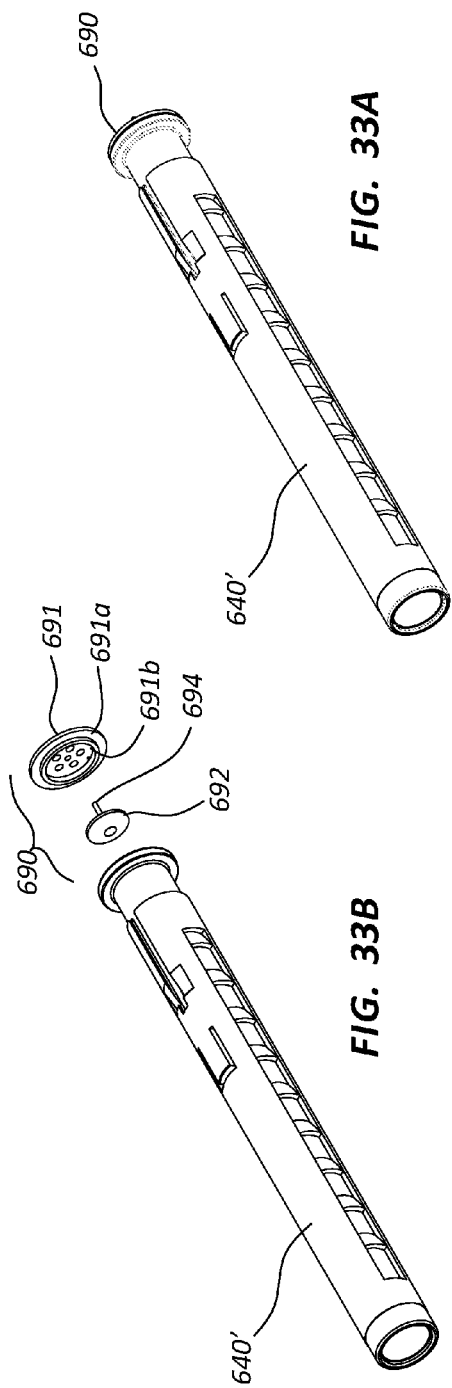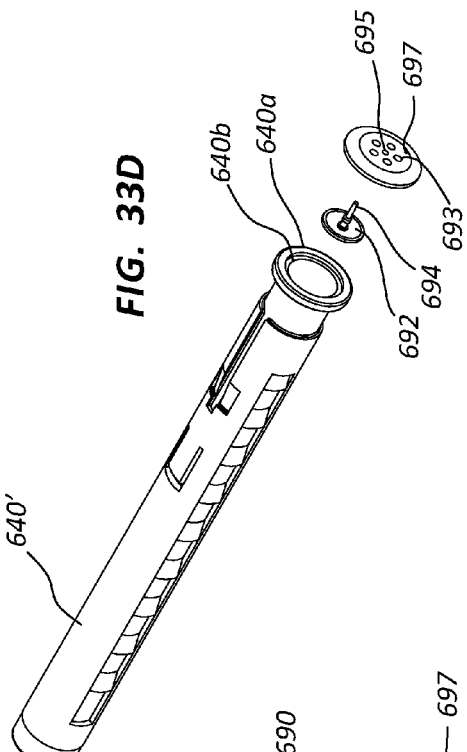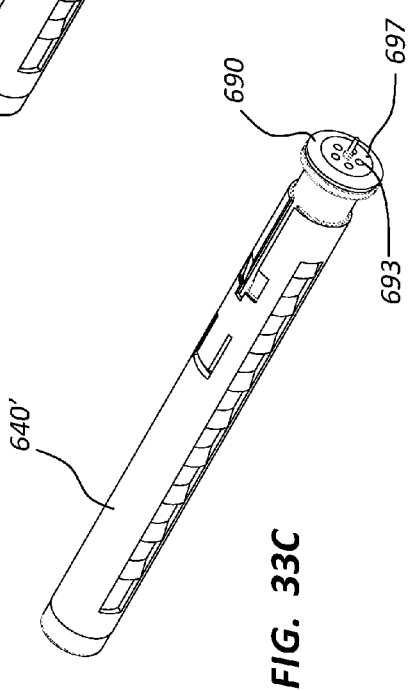

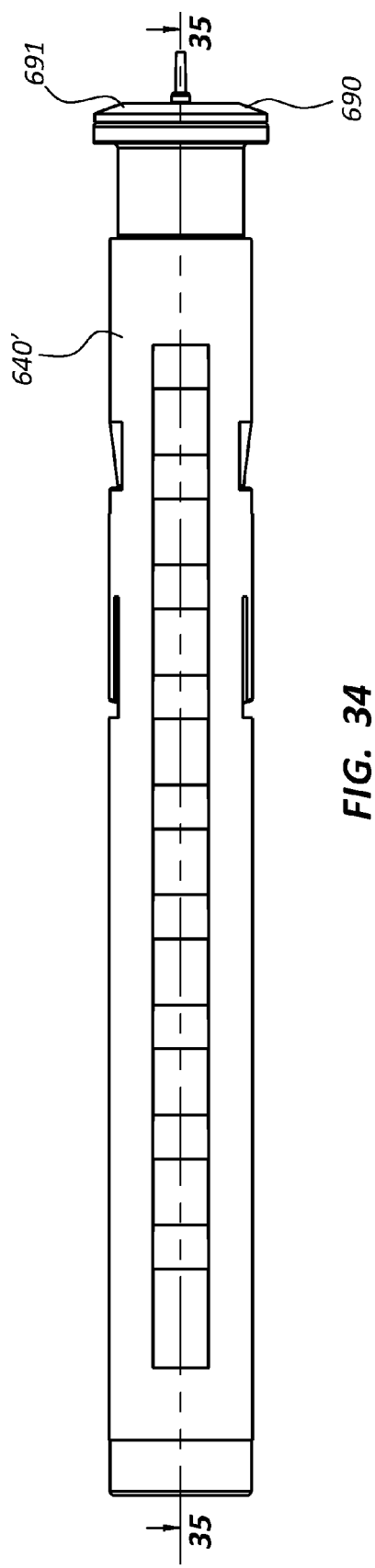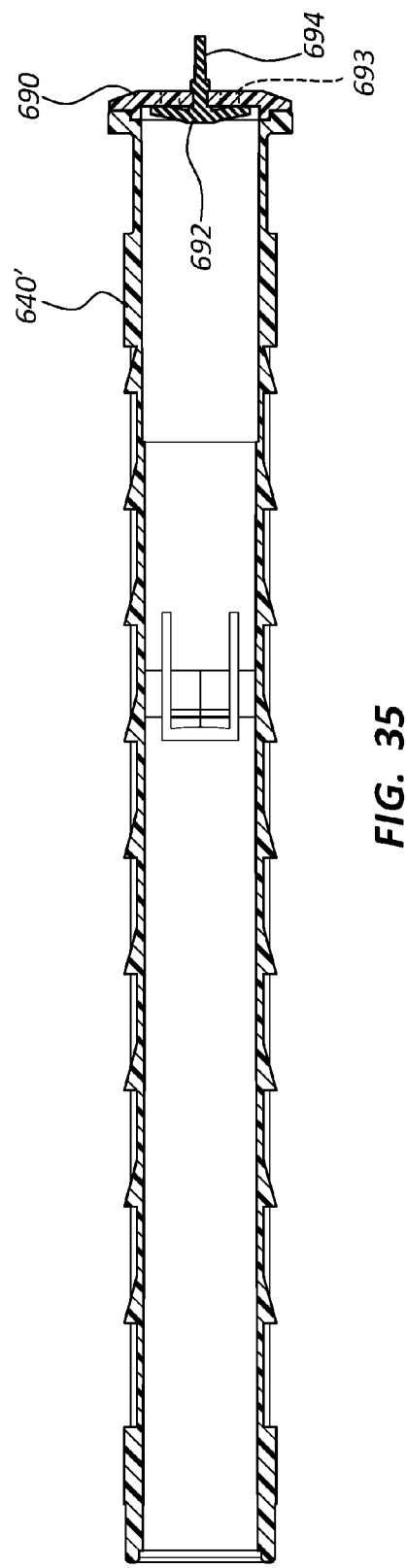
FIG. 34
FIG. 35

VARIABLE DISPLACEMENT INFLATION DEVICES AND METHODS OF USE

CROSS-REFERENCE TO RELATED APPLICATIONS

Under 35 U.S.C. §119(e), this application claims the benefit of U.S. Provisional Patent Application No. 61/704,299, entitled "VARIABLE DISPLACEMENT INFLATION DEVICE AND METHOD OF USE," filed Sep. 21, 2012, the contents of which are hereby incorporated herein by reference in their entirety.

TECHNICAL FIELD

The present disclosure relates generally to devices used to pressurize, depressurize, or otherwise displace fluid, particularly in medical devices. For example, the present disclosure relates to devices used to pressurize, depressurize, or otherwise displace fluid along a line in order to inflate or deflate a medical device, such as a balloon. In some embodiments, inflation devices within the scope of this disclosure may comprise multiple plungers configured to facilitate inflation at relatively high pressure. Further, inflation devices within the scope of this disclosure may be configured to selectively lock or deploy certain plungers to control the forces required to reach particular inflation pressures.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 4 is a top view of the inflation device of FIG. 1.

FIG. 5 is a front view of the inflation device of FIG. 1.

FIG. 6 is a cross-sectional view of the inflation device of FIG. 4, taken through plane 6-6.

FIG. 6A is a detail view of a portion of the inflation device of FIG. 6.

FIG. 6B is a detail view of another portion of the inflation device of FIG. 6.

FIG. 7 is a cross-sectional view of the inflation device of FIG. 5, taken through plane 7-7.

FIG. 7A is a detail view of a portion of the inflation device of FIG. 7.

FIG. 7B is a detail view of another portion of the inflation device of FIG. 7.

FIG. 8A is a first cross-sectional view of the inflation device of FIG. 1 in a first position.

FIG. 8B is a second cross-sectional view of the inflation device of FIG. 8A.

FIG. 9A is a first cross-sectional view of the inflation device of FIG. 1 in a second position.

FIG. 9B is a second cross-sectional view of the inflation device of FIG. 9A.

FIG. 11A is a first cross-sectional view of the inflation device of FIG. 1 in a fourth position.

FIG. 11B is a second cross-sectional view of the inflation device of FIG. 11A.

FIG. 12A is a first cross-sectional view of the inflation device of FIG. 1 in a fifth position.

FIG. 12B is a second cross-sectional view of the inflation device of FIG. 12A.

FIG. 13A is a first cross-sectional view of the inflation device of FIG. 1 in a sixth position.

FIG. 13B is a second cross-sectional view of the inflation device of FIG. 13A.

FIG. 14A is a first cross-sectional view of the inflation device of FIG. 1 in a seventh position.

FIG. 14B is a second cross-sectional view of the inflation device of FIG. 14A.

FIG. 15A is a first cross-sectional view of the inflation device of FIG. 1 in an eighth position.

FIG. 15B is a second cross-sectional view of the inflation device of FIG. 15A.

FIG. 19 is a top view of the inflation device of FIG. 16.

FIG. 20 is a front view of the inflation device of FIG. 16.

FIG. 21 is a cross-sectional view of the inflation device of FIG. 19, taken through plane 21-21.

FIG. 22 is a cross-sectional view of the inflation device of FIG. 20, taken through plane 22-22.

FIG. 29 is a top view of the inflation device of FIG. 26.

FIG. 30 is a side view of the inflation device of FIG. 26.

FIG. 31 is a cross-sectional view of the inflation device of FIG. 29, taken through plane 31-31.

FIG. 32 is a cross-sectional view of the inflation device of FIG. 30, taken through plane 32-32.

FIG. 33A is a rear exploded perspective view of one embodiment of a valve and one embodiment of an intermediate plunger for use with an inflation device.

FIG. 33B a rear assembled perspective view of one embodiment of a valve and one embodiment of an intermediate plunger for use with an inflation device.

FIG. 33C is a rear front exploded perspective view of one embodiment of a valve and one embodiment of an intermediate plunger for use with an inflation device.

FIG. 33D is a front assembled perspective view of one embodiment of a valve and one embodiment of an intermediate plunger for use with an inflation device.

FIG. 34 is a side view of the assembled intermediate plunger and valve illustrated in FIG. 33B and FIG. 33D.

FIG. 35 is a cross-sectional view of the assembly of FIG. 34 taken through plane 35-35.

DETAILED DESCRIPTION

Figure 1:
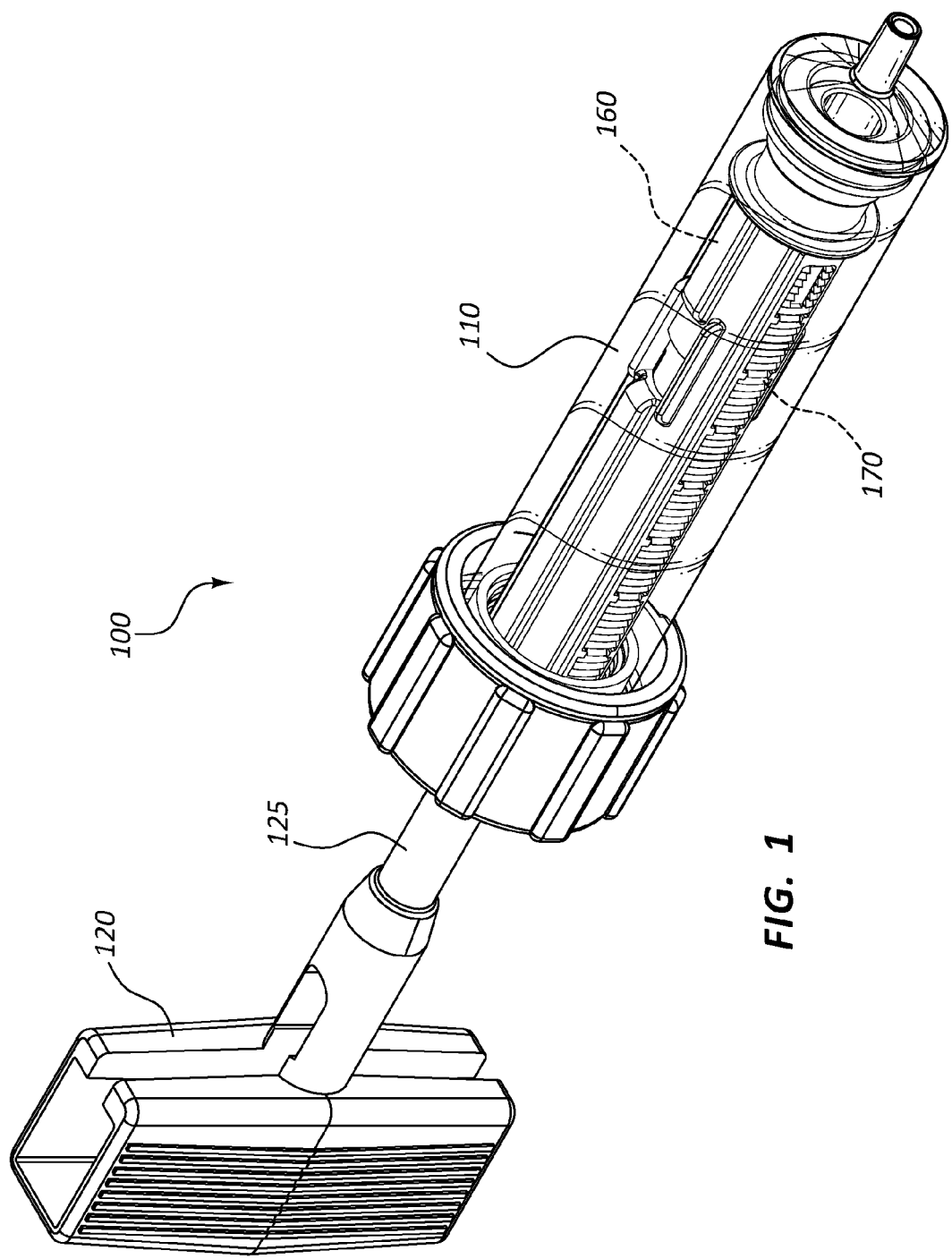
FIG. 1 is a front perspective view of an inflation device.

Inflation devices may be configured for use in connection with devices or procedures utilizing high inflation pressures. For example, certain procedures, such as valvuloplasty, may be performed at pressures up to, and exceeding, 6-12 ATM. Simultaneously, displacement of relatively large volumes of fluid may also be a part of such procedures. When using a single-plunger syringe-type inflation device, larger diameter syringes may be selected in order to meet fluid displacement needs; however, use of large diameter syringes may also necessitate high input forces in order to obtain high pressure. In other words, because the input force required to reach a particular pressure is the product of the pressure and the effective surface area of the plunger acting on the fluid, large syringes may require large input forces. A smaller diameter syringe may require less force at high pressures, but may not be able to supply sufficient fluid volume without requiring the syringe to be particularly long. In some instances, a practitioner may utilize a 60 ml syringe, for example, to inflate a valvuloplasty balloon to 6-12 ATM during therapy. Such pressure may require in excess of 80 lbs of input force to the handle of a single-plunger syringe.

As further detailed below, an inflation device may be configured to utilize a larger plunger to displace large volumes of fluid at low pressure, and a smaller plunger to pressurize the fluid. In some embodiments, multiple plungers may be coupled to a single handle, including embodiments wherein the inflation device is configured to automatically toggle between a large plunger and a smaller plunger. Further, the inflation device may be configured to lock one or more plungers in place while another plunger is being utilized. As further detailed below, use of a smaller plunger to pressurize the fluid may result in a substantial decrease in the force required to pressurize a medical device. For example, generally pressurizing a 60 ml syringe to 6-7 ATM may require in excess of 80 lbs; this force may be reduced to 15 lbs or less when using a multiple plunger device.

Some inflation devices may be configured for high pressure inflation through the use of locking mechanisms or advancement threads. However, certain therapies may require rapid inflation/deflation of a medical device, which may not be possible through the use of a locking syringe. For example, in some valvuloplasty procedures, a practitioner may inflate and pressurize a balloon within a heart valve between heartbeats, then depressurize the balloon during a heartbeat, and again re-pressurize the balloon after the heartbeat. Attempting to reach high pressures through the use of threads may not be possible in such short time frames.

It will be readily understood by one of ordinary skill in the art having the benefit of this disclosure that the components of the embodiments, as generally described and illustrated in the figures herein, could be arranged and designed in a wide variety of configurations. Thus, the following more detailed description of various embodiments, as represented in the figures, is not intended to limit the scope of the disclosure, but is merely representative of various embodiments. While the various aspects of the embodiments are presented in the drawings, the drawings are not necessarily drawn to scale unless specifically indicated.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to the syringe portion of an inflation device, the proximal end of the syringe refers to the end nearest the handle and the distal end refers to the opposite end, the end nearest the inlet/outlet port of the syringe. Thus, if at one or more points in a procedure a physician changes the orientation of a syringe, as used herein, the term "proximal end" always refers to the handle end of the syringe (even if the distal end is temporarily closer to the physician).

"Fluid" is used in its broadest sense, to refer to any fluid, including both liquids and gasses as well as solutions, compounds, suspensions, etc., which generally behave as a fluid.

As used herein, the "effective surface area" of a component is used in connection with pressure acting on a surface area. The effective surface area of a component is equivalent to the surface area of a flat surface with the same net force from the pressure acting on the surface. In other words, angled surfaces may have components of pressure that oppose each other and therefore cancel out. The net pressure on an angled surface generates the same force as the total pressure acting on a flat surface having a total surface area that equals the effective surface area of the angled surface.

FIGS. 1-15B illustrate different views of an inflation device. Certain components may be shown in multiple views, but not discussed in connection with every view. Disclosure provided in connection with any figure is relevant and applicable to disclosure provided in connection with any other figure. FIGS. 16-22 illustrate another embodiment of an inflation device. FIGS. 23-38 illustrate views of additional embodiments of inflation devices. Any of the inflation devices shown or discussed herein may be used in connection with any variety of medical devices configured for inflation or fluid flow, such as balloons, bags, lines, and so forth.

FIG. 1 is a front perspective view of an inflation device 100. This view illustrates an assembled configuration of the inflation device 100, with a variety of components indicated by reference numerals. More detail regarding each of these components is provided in connection with subsequent figures. As shown in FIG. 1, the inflation device 100 may comprise a body member, such as syringe body 110, and a handle 120. A shaft 125 may extend from the handle 120 and into the syringe body 110. As further detailed below, manipulation of the handle 120 with respect to the syringe body 110 may displace fluid within the inflation device 100. Also as detailed below, a locking sleeve 160 and locking rails 170 may be configured to selectively toggle between multiple plungers within the inflation device 100.

Figure 2:
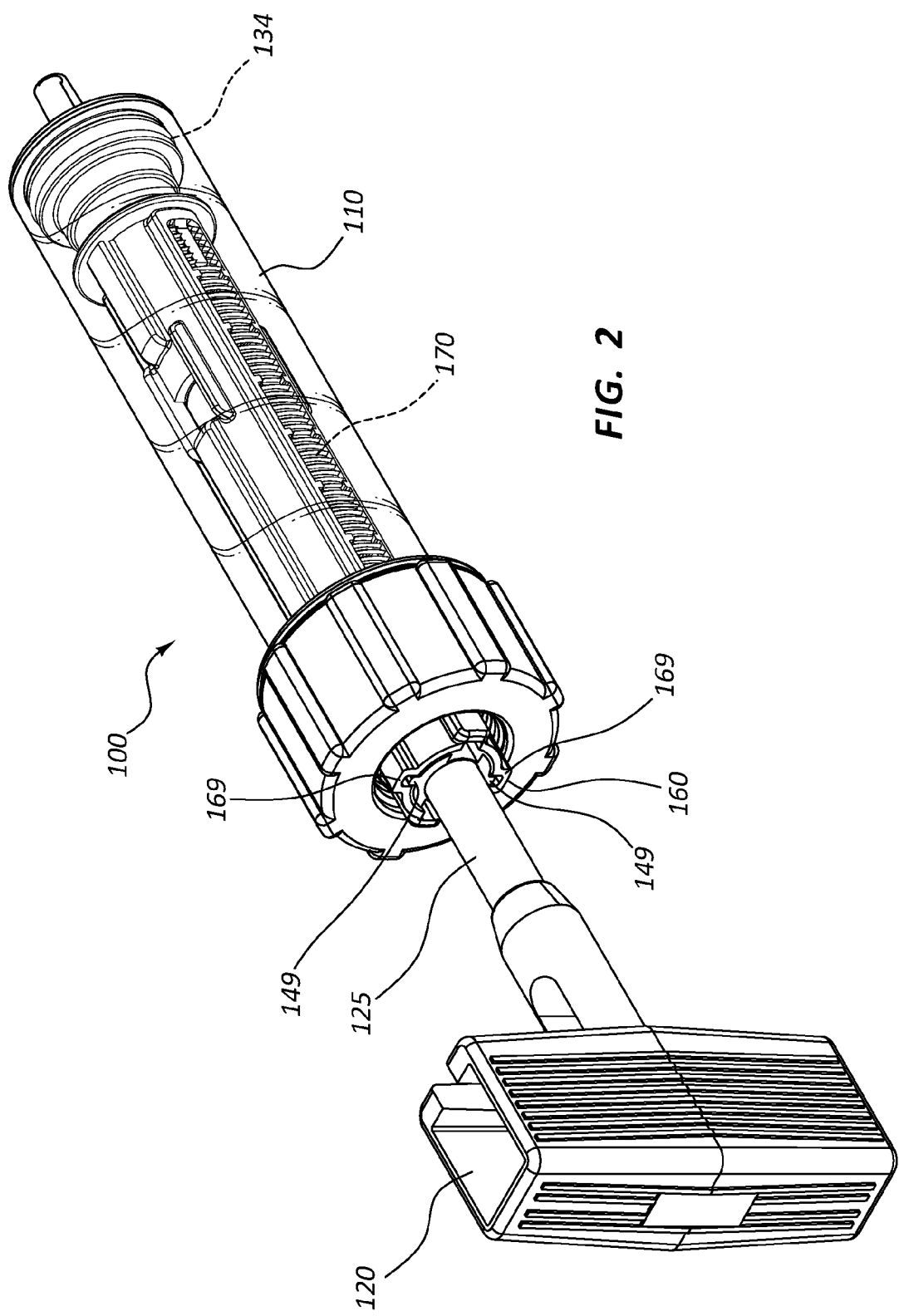
FIG. 2 is a rear perspective view of the inflation device of FIG. 1.

FIG. 2 is a rear perspective view of the inflation device 100 of FIG. 1. In the view of FIG. 2, the shaft 125 is shown extending from the handle 120 and into the locking sleeve 160 and syringe body 110. Further, an outer plunger seal 134 is shown in connection with the syringe body 110. The outer plunger seal 134 may be configured, in connection with other components, to displace fluid within the syringe body 110. The locking rails 170 are also shown.

Figure 3:
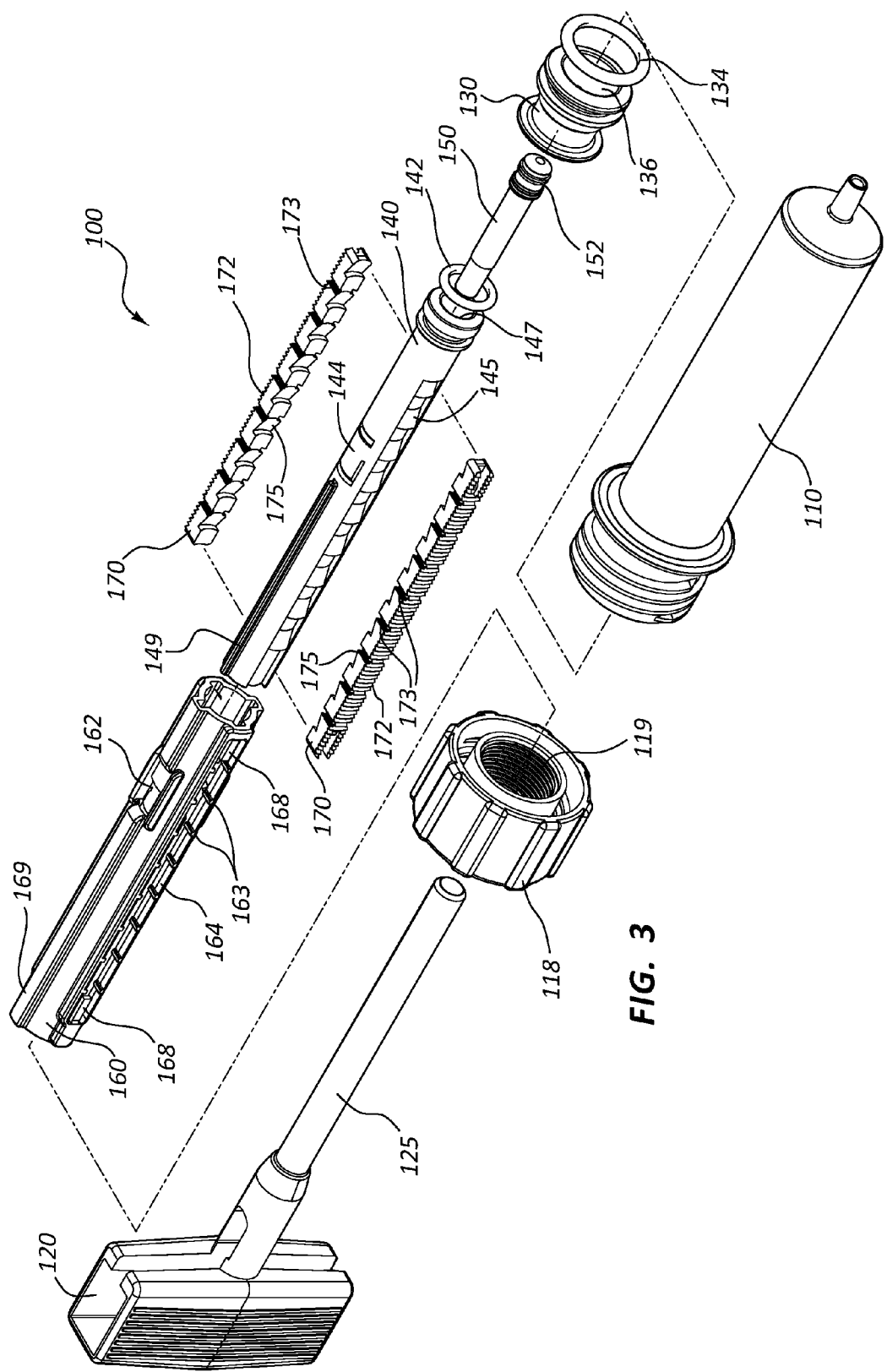
FIG. 3 is an exploded view of the inflation device of FIG. 1.

FIG. 3 is an exploded view of the inflation device 100 of FIG. 1. As illustrated in FIG. 3, the shaft 125 may extend from the handle 120 and interact with other components within the syringe body 110. A cap 118 may be coupled to the proximal end of the syringe body 110. The cap 118 may comprise cap locking threads 119 configured to interact with, and selectively secure, other components of the assembly.

The inflation device 100 may further comprise a volume plunger that, in the illustrated embodiment, is comprised of an outer plunger 130 and an intermediate plunger 140. The volume plunger (130, 140) may be configured to displace a larger volume of fluid in response to displacement of the handle 120 as compared to the inner plunger 150. The outer plunger 130 and intermediate plunger 140 may be collectively referred to as the "volume plunger" (130, 140) in some descriptions herein. For clarity regarding reference numerals, the "volume plunger" will simply be recited in connection with both reference numerals (130, 140) of the subcomponents, with the numerals in parentheses. The outer plunger 130 may be coupled to an outer plunger seal 134 configured to provide a fluid seal between the inside diameter of the syringe body 110 and the outer plunger 130. The outer plunger 130 may be configured as a substantially hollow component, defining an interior portion 136 therein.

The intermediate plunger 140 may be configured to be disposed within the interior portion of the outer plunger 130. An intermediate plunger seal 142 may be disposed such that it provides a fluid seal between the inside diameter of the interior portion 136 and the intermediate plunger 140. The intermediate plunger 140 may also comprise an interior portion 147 within a portion of the intermediate plunger 140.

In the illustrated embodiment, the intermediate plunger 140 and the outer plunger 130 are both illustrated in connection with seals 134, 142, which may comprise o-rings. In other embodiments, the plungers 130, 140 may be comprised of a material (such as an elastomeric material) that is self-sealing; thus, the seals 134, 142 may be integrally formed with the plungers 130, 140.

An inner plunger 150 may be disposed within the interior portion 147 of the intermediate plunger 140. The inner plunger 150 may be configured with an inner plunger seal 152, configured to provide a fluid seal between the inner plunger 150 and the inside diameter of the interior portion 147 of the intermediate plunger 140. As with the other plungers, the inner plunger seal 152 may be integrally formed with the inner plunger 150 or may comprise a separate component such as an o-ring.

When assembled together, the outer plunger seal 134, the outer plunger 130, the intermediate plunger seal 142, the intermediate plunger 140, and the inner plunger 150 may collectively form a fluid seal within the syringe body 110. Thus, advancing these components, collectively or individually, may be configured to displace fluid within the syringe body 110.

The inflation device 100 may further comprise a locking sleeve 160 and locking rails 170 configured to couple one or more of the outer plunger 130 and the intermediate plunger 140 to the syringe body 110. The locking sleeve 160 may comprise slots 164 configured to receive the locking rails 170. Mating grooves 173 and ridges 163 on these components may be disposed such that movement of the locking rails 170 with respect to the locking sleeve 160 is constrained. For example, in the illustrated embodiment, these grooves 173 and ridges 163 constrain the locking rails 170 such that they may only move radially inward or outward in the slots 164. In other embodiments these features may allow different types of relative motion. For example the grooves 173 and ridges 163 may be disposed at an angle to the radially outward direction.

The locking rails 170 may comprise locking rail threads 172 configured to engage the cap locking threads 119 of the cap 118. In other embodiments other features, such as mating grooves and ridges, may be used in place of threads. The locking rails 170 may be configured to move in connection with locking rail angled surfaces 175 that interact with intermediate plunger angled surfaces 145. The relative position on these components may be configured to selectively engage or disengage the locking rail threads 172 and the cap locking threads 119.

In some embodiments, one or more axial tabs may be coupled to the locking rails 170. For example, such tabs may be molded with the locking rails 170 and may be disposed on one or more of the angled surfaces 175. Such tabs may be configured to pass through slots the intermediate plunger 140 and communicate with the shaft 125 and the inner plunger 150. The tabs may be configured to prevent the locking rails 170 from releasing (or moving radially inward) from the threads (or grooves) while the shaft 125 and inner plunger 150 are advanced distally. The outer surface of the shaft 125 may be configured with grooves, or a reduced diameter along a portion of the shaft 125, to accommodate the tabs when the locking rails 170 are in the unlocked position. An embodiment with tabs may be configured such that the shaft 125 must be pulled back proximally to unlock the locking rails 170 and locking sleeve 160 to advance or retract the outer plunger 130. Thus, in the illustrated embodiment, the locking mechanism may be activated and maintained by pressure; in an embodiment utilizing tabs as described above, the locking mechanism may be activated by pressure and maintained by pressure and the distal travel of the shaft 125 and inner plunger 150.

As illustrated in FIGS. 2 and 3, the locking sleeve 160 may include a guide groove 169 configured to mate with a guide rail 149 formed on the intermediate plunger 140. The guide rail 149 and the guide groove 169 may facilitate alignment during assembly of the inflation device 100 and may also resist rotation of the intermediate plunger 140 and the locking sleeve 160 relative to each other.

The locking sleeve 160 may be disposed around the intermediate plunger 140 when the inflation device 100 is assembled. Windows 162 in the locking sleeve 160 may interact with engagement arms 144 of the intermediate plunger 140 to selectively engage these and adjacent components. Additionally, one or more biasing elements 168 may be provided in connection with the locking sleeve 160 and the other components. It will be appreciated by one skilled in the art and having the benefit of this disclosure that many features, such as the windows 162, engagement arms 144, slots 164, and so forth, may be arranged symmetrically around the circumference of the inflation device 100. As is further shown in the cross-sectional views discussed below, in the illustrated embodiment many of these components are present in pairs. In other embodiments, additional iterations of any of these components may be disposed around the inflation device.

The locking sleeve 160, the locking rails 170, the inner plunger 150, the intermediate plunger 140, and the outer plunger 130 may each interact to vary which components are longitudinally displaced in response to displacement of the handle 120 with respect to the syringe body 110. The interactions of these components are further detailed in connection with the figures described below, including the cross-sectional views in FIGS. 6-7B. It will be appreciated by one skilled in the art and having the benefit of this disclosure that other combinations of components and parts may be configured in differing ways to control these components. Inflation devices configured to selectively displace multiple plungers, including devices wherein the plungers are displaced by a single handle, are within the scope of this disclosure, notwithstanding differences in the particular components and mechanisms utilized therein.

FIG. 4 is a top view of the inflation device 100, and FIG. 5 is a front view of the inflation device 100 of FIG. 1. FIGS. 4 and 5 illustrate the handle 120 and shaft 125 of the inflation device, as well as the cap 118 and the syringe body 110. Further, the relative positions of the locking sleeve 160, locking rails 170, and window 162 are shown. FIGS. 4 and 5 further include section planes 6-6 and 7-7, the cross-sectional planes of FIGS. 6 and 7.

FIGS. 4 and 5 further illustrate a volume reservoir 114 defined by the inside diameter of the syringe body 110 as well as by the seals and plungers (the outer plunger seal 134, the outer plunger 130, the intermediate plunger seal 142, the intermediate plunger 140, and the inner plunger 150, all of FIG. 3) that may collectively form a fluid seal within the syringe body 110. Thus, displacing these seals and plungers with respect to the syringe body 110 may displace fluid within the volume reservoir 114. Such displacement may force fluid into or out of the reservoir 114 and/or pressurize fluid within the volume reservoir and anything in fluid communication therewith.

FIG. 6 is a cross-sectional view of the inflation device 100 of FIG. 4, taken through plane 6-6. The cap 118 and syringe body 110 are shown. In the illustrated embodiment, the shaft 125 extends distally from the handle 120 and the shaft 125 is fixedly coupled to the inner plunger 150. The inner plunger 150 is disposed within the interior portion 147 of the intermediate plunger 140. The inner plunger seal 152 is positioned to provide a fluid seal between the inside diameter of the interior portion 147 of the intermediate plunger 140 and the inner plunger 150. The intermediate plunger 140 is disposed within the interior portion 136 of the outer plunger 130. The intermediate plunger seal 142 is disposed to provide a fluid seal between the intermediate plunger 140 and the inside diameter of the interior portion 136 of the outer plunger 130. Finally, the outer plunger seal 134 provides a fluid seal between the inside diameter of the syringe body 110 and the outer plunger 130.

Thus, the seals and plungers provide a fluid seal to define the volume reservoir 114 in connection with the syringe body 110. In some configurations, these plungers and seals (150, 152, 140, 142, 130, 134) may be configured to be advanced or retracted together, or substantially together, in order to displace fluid within the volume reservoir 114. The force required to advance these components together is essentially the sum of the net pressure forces acting on each component (neglecting friction, for example). In other words, the effective surface area of each component multiplied by the pressure within the volume reservoir 114 is essentially equivalent to the force required to advance the components collectively.

The inflation device 100 may be disposed in a configuration wherein all the plungers and seals (150, 152, 140, 142, 130, 134) are configured to be advanced or retracted substantially together. As further detailed below, this configuration is the "unlocked" configuration, meaning the volume plunger (130, 140), comprising the outer plunger 130 and that intermediate plunger 140, is unlocked with respect to the syringe body 110. Also, it will be understood by one skilled in the art and having the benefit of this disclosure that displacement or locking of a plunger similarly displaces or locks the seal or seals associated therewith. Additionally, as further described below, in the unlocked configuration, displacement of the handle, proximally or distally, may displace both the volume plunger (130, 140) and the inner plunger 150. In the unlocked configuration, the inner plunger 150 may be coupled to the volume plunger (130, 140). This configuration may allow a practitioner to displace a large volume of fluid quickly, for example, to initially inflate a balloon. In some embodiments, this configuration may only be utilized to fill the balloon or other device in relatively low pressure conditions.

The inflation device may also be disposed in a second configuration, the "locked configuration" in which the volume plunger (130, 140) is coupled to the syringe body 110. The inner plunger 150 may be decoupled from the volume plunger (130, 140) in the locked configuration, such that displacement of the handle 120 proximally or distally displaces the inner plunger 150 but not the volume plunger (130, 140). In this configuration, the inner plunger 150 may be allowed to move longitudinally within the interior portion 147 of the intermediate plunger 140. The inner plunger 150 and interior portion 147 may thus define a pressure reservoir 138 in fluid communication with the volume reservoir 114. As the inner plunger 150 is advanced within the pressure reservoir, the inner plunger 150 may thus increase the pressure within the pressure reservoir 138 (and volume reservoir 114) by displacing fluid. The force required to advance the inner plunger is essentially equivalent to the pressure in the pressure reservoir 138 multiplied by the effective surface area of the inner plunger 150. Thus, displacing only the inner plunger 150, as opposed to the inner plunger 150 and the volume plunger (130, 140) may decrease the force required to increase the pressure within the pressure and volume reservoirs 138, 114.

In some embodiments the inflation device 100 may be configured such that a user can select the locked or unlocked configurations manually. In other embodiments, the inflation device 100 may be configured to automatically change configurations in response to pressure or forces on components of the inflation device 100. The embodiment illustrated in FIGS. 1-15B is configured to automatically change configurations, as detailed below.

The inflation device 100 of FIG. 6 is illustrated in the unlocked configuration. The inner plunger 150 is fixedly coupled to the shaft 125 of the handle 120. Further, as shown in FIG. 6A, a detail view of a portion of the inflation device 100 of FIG. 6, the distal end of the shaft 127 may be disposed such that it contacts the engagement arm 144 of the intermediate plunger 140. In the unlocked configuration, a portion of the locking sleeve 160 prevents the engagement arm 144 from expanding radially; thus, distal advancement of the handle 120 and shaft 125 distally advances the intermediate plunger 140 in the unlocked configuration.

Additionally, as shown in FIG. 6B, a detail view of another portion of the inflation device 100 of FIG. 6, in the illustrated embodiment the locking sleeve 160 and intermediate plunger 140 are releasably coupled to each other in the unlocked configuration by a detent 166, 146. More specifically, a recess portion 146 and a nub portion 166 of a detent couple the locking sleeve 160 and the intermediate plunger 140. The nub portion 166 of the detent may be positioned on a compliant nub arm 165 configured to deform outwardly (thus decoupling the intermediate plunger 140 and the locking sleeve 160) in response to a force or forces on these components as further detailed below. In the unlocked configuration, however, the nub arm 165 maintains the position of the nub portion 166 within the recess portion 146.

Referring again to FIG. 6, the outer plunger 130 may be fixedly coupled to the locking sleeve 160. Thus, in the unlocked configuration, advancement of the handle 120 advances the inner plunger 150 (as it is fixedly coupled to the shaft 125), the intermediate plunger 140 (due to the interaction for the distal end of the shaft 127 and the engagement arm 144), the locking sleeve 160 (due to the interaction of the nub 166 and recess 146 detent portions), and the outer plunger 130 (as it is fixedly coupled to the locking sleeve 160).

Additionally, in the unlocked configuration, retracting the handle 120 retracts the inner plunger 150 because it is fixedly coupled to the shaft 125. Further, the inner plunger seal 152 may comprise a flange configured to interact with a distal shoulder 148 of the intermediate plunger 140. Thus, retracting the handle 120 in the unlocked configuration also retracts the intermediate plunger 140. Further, retraction of the intermediate plunger 140 retracts the locking sleeve 160 (due to the interaction of the nub 166 and recess 146 detent portions), and the outer plunger 130 (as it is fixedly coupled to the locking sleeve 160).

Therefore, in the unlocked configuration, a practitioner may displace the volume plunger (130, 140) and the inner plunger 150 simultaneously, proximally, or distally by displacing the handle 120. This may allow a practitioner to initially fill or inflate a medical device, such as a balloon, quickly by displacing a large effective surface area. In some embodiments, a practitioner may initially inflate, but not substantially pressurize, a medical device with the inflation device in the unlocked configuration.

In the unlocked configuration, pressure within the volume reservoir will exert a proximal force on the inner plunger 150, the intermediate plunger 140, and the outer plunger 130. Proximal force on the inner plunger 150 will be transferred to the handle 120 via the shaft 125; thus, as long as a sufficient reactionary force (e.g., due to the practitioner's hand) remains on the handle 120, pressure within the volume reservoir 114 will not displace the inner plunger 150 proximally. Similarly, a proximal pressure force on the intermediate plunger 140 will be transferred to the handle 120 by contact of the engagement arms 144 with the distal end of the shaft 127. Again, a reactionary force on the handle 120 will maintain the position of the intermediate plunger 140.

A proximal pressure force on the outer plunger 130, however, will be transferred to the locking sleeve 160, and then to the nub 166 and recess 146 detent portions. Once the force on the outer plunger 130 is sufficient to overcome the force on the nub arms 165 maintaining the nub 166 within the recess 146, the outer plunger 130 and locking sleeve 160 will move proximally with respect to the intermediate plunger 140, the inner plunger 150, the handle 120, and the syringe body 110. This displacement of the locking sleeve 160 with respect to the other components shifts the inflation device 100 from the unlocked configuration to the locked configuration. In other embodiments, other types or configurations of detents, locking features, ribs, catches, frangible members, or the like may be utilized to associate the locking sleeve 160 and the intermediate plunger 140 and other components.

Interaction of the window hook 161 of the locking sleeve 160 and the proximal shoulder 141 of the intermediate plunger 140 may limit the extent to which the locking sleeve 160 may move with respect to the other components. Once the locking sleeve 160 shifts proximally to the locked configuration, the windows 162 of the locking sleeve 160 move into alignment with the engagement arms 144 of the intermediate plunger 140. As shown in FIG. 6A, the engagement arms 144 may be configured with an angled surface at the point of interaction with the distal end of the shaft 127. Thus, the reactionary force acting on the handle 120 and shaft 125 will cause the engagement arms 144 to expand radially outward due to the interaction of this angled surface and the distal end of the shaft 127, which may have a larger diameter than the inner plunger 150. In the locked configuration, the window hook 161 of the locking sleeve 160 may be constrained between the proximal shoulder 141 and the expanded engagement arms 144 of intermediate plunger 140, thus releasably coupling the intermediate plunger 140 to the locking sleeve 160.

Thus, in the unlocked configuration, proximal displacement of the handle 120 displaces only the inner plunger 150, as the engagement arms 144 are no longer constrained into contact with the distal end of the shaft 127. Once the inner plunger 150 is advanced, any retraction of the handle 120 will retract only the inner plunger 150, as long as the inner plunger 150 is not sufficiently retracted to cause the inner plunger seal 152 to contact the distal shoulder 148 of the intermediate plunger 140. In other words, the inner plunger 150 may move within the pressure reservoir 138 in response to inputs at the handle 120 in the locked configuration.

In the locked configuration, the locking sleeve 160 may be releasably coupled to the syringe body 110. FIG. 7 is a cross-sectional view of the inflation device 100 of FIG. 5, taken through plane 7-7. FIG. 7 illustrates the locking rails 170. The locking rails 170 may be configured with angled surfaces 175 configured to mate with angled surfaces 145 of the intermediate plunger 140. Further, the locking rails 170 may be constrained to only move radially with respect to the locking sleeve 160 due to the interaction of the mating grooves (173 of FIG. 3) and ridges (163 of FIG. 3) of these components. Thus, displacement of the locking sleeve 160 proximally with respect to the intermediate plunger 140—as the inflation device shifts to the locked configuration—causes the locking rails 170 to move proximally with respect to the intermediate plunger 140 as well. As the locking rails 170 are thus displaced, interaction of the angled surfaces 175 of the locking rails 170 and the angled surfaces 145 of the intermediate plunger 140 displace the locking rails 170 radially outward. FIG. 7A, a detail view of a portion of the inflation device 100 of FIG. 7, illustrates the contact of these surfaces in the unlocked configuration. As the locking rails expand outward, the locking rail threads 172 engage the cap locking threads 119, shown in FIG. 7.

Thus, in the locked configuration, the locking rails 170 are locked with respect to the cap 118 and syringe body 110. This, in turn, locks the locking sleeve 160 with respect to the syringe body 110 (due to the interaction of the mating grooves (173 of FIG. 3) and ridges (163 of FIG. 3)). The outer plunger 130 is similarly locked as it is fixedly coupled to the locking sleeve 160. Finally, the intermediate plunger 140 is locked due to the window hook 161 of the locking sleeve 160 being constrained between the proximal shoulder 141 and the expanded engagement arms 144 of intermediate plunger 140.

FIG. 7B, a detail view of another portion of the inflation device 100 of FIG. 7, illustrates one of the biasing elements 168 of the locking sleeve 160. The biasing elements 168 may comprise compliant tabs or extensions that interact with the thread rails 170. The biasing elements 168 may be configured to provide a biasing force tending to keep the locking rails 170 from expanding radially until the biasing force is overcome, and tend to return the locking raids 170 radially inward when the device is shifted from a locked to an unlocked configuration.

Again, in the locked configuration a practitioner may displace the inner plunger 150 within the pressure reservoir 138 to pressurize or depressurize a medical device. For example, a practitioner may inflate (but not pressurize) a balloon in the unlocked configuration. In the unlocked configuration the practitioner may then pressurize and depressurize the balloon multiple times without fully deflating the balloon or toggling the device to the unlocked configuration. This may be used in therapies where a balloon or other device must be pressurized and depressurized multiple times during a treatment (for example, between heartbeats).

When a practitioner desires to shift the inflation device 100 from the locked configuration to the unlocked configuration, the practitioner may proximally displace the handle 120 (and thus the inner plunger 150) until the distal end of the shaft 127 moves proximally beyond the engagement arms 144. Once the distal end of the shaft 127 is no longer forcing the engagement arms 144 radially outward, the compliant engagement arms 144 may return radially inward, again as the proximal end of the inner plunger 150 may have a smaller diameter than the distal end of the shaft 127. Interaction of the inner plunger seal 152 and the distal shoulder 148 of the intermediate plunger 140 may then cause proximal displacement of the handle 120 (and thus the inner plunger 150) to proximally displace the intermediate plunger 140 with respect to the locking sleeve 160, moving the engagement arms 144 out of alignment with the window 162, and reengaging the nub 166 and recess 146 detent portions. Further, the angled surfaces 145 of the intermediate plunger 140 move with respect to the angled surfaces 175 of the locking rails 170, allowing the biasing elements 168 to radially retract the locking rails 170 and disengaging the locking rails 170 and cap 118. The inflation device 100 is thus returned to the unlocked configuration and ready to be used in this configuration.

The inflation device 100 may thus be shifted between the locked and unlocked configurations during a single therapy, reused in one or both configurations in subsequent therapies, and so forth. Further, the components shown and described in the disclosure above may be alternatively formed in various shapes or configurations in other embodiments. Particular angles, shapes, or geometries shown are thus not intended to be limiting, but rather illustrate potential embodiments of the components. Further, any component described as "fixedly coupled" to another component may be integrally formed in some embodiments.

FIGS. 8A-15B illustrate various positions of the inflation device 100 during an exemplary procedure. Thus, while FIGS. 6-7B illustrated only the unlocked configuration and described the locked configuration, these subsequent figures show various stages of both configurations. Each of FIGS. 8A-15B illustrates the mechanism in each position in two cross-sections, one denoted "A" and one denoted "B." The "A" cross-sections are along a plane analogous to plane 6-6 of FIG. 4, and the cross-sections denoted "B" are taken along a plane analogous to plane 7-7 of FIG. 5.

FIGS. 8A and 8B are cross-sectional views of the inflation device 100 of FIG. 1 in a first position. Specifically, the inflation device 100 is illustrated in the unlocked configuration, with the handle 120, the volume plunger (130, 140), and the inner plunger 150 all drawn back with respect to the syringe body 110. The volume reservoir 114 is also shown. As the device is in the unlocked configuration, the engagement arms 144 are not aligned with the windows 162 of the locking sleeve 160 and the recess portion 146 and nub portions 166 of the detents are engaged. The locking rail angled surfaces 175 and the intermediate plunger angled surfaces 145 are disposed such that the locking rail threads 172 of the locking rails 170 are not engaged with the cap locking threads 119. The biasing elements 168 are not deflected outward.

As described above, in the unlocked configuration, displacement of the handle 120 with respect to the syringe body 110 displaces the volume plunger (130, 140) and the inner plunger 150. In some exemplary procedures, a practitioner may first obtain the inflation device 100 in the configuration shown in FIGS. 8A and 8B, prior to beginning a therapy.

In some therapies, the physician may then advance the volume plunger (130, 140) and the inner plunger 150 (again by advancing the handle 120) in order to evacuate any fluid from the volume reservoir 114. FIGS. 9A and 9B are cross-sectional views of the inflation device 100 of FIG. 1 in a second position, with the volume plunger (130, 140) and the inner plunger 150 advanced within the syringe body 110 as compared to the first position of FIGS. 8A and 8B. The handle 120, the outer plunger 130, the intermediate plunger 140, the inner plunger 150, the locking sleeve 160, and the locking rails 170, as well as their related components—the shaft 125, the distal end of the shaft 127, the engagement arms 144, the windows 162, the recess portion 146 and nub portions 166 of the detent, the angled surfaces of the intermediate plunger 145 and the angled surfaces of the locking rails 175, and the biasing elements 168—are in the same relative positions to each other as described in connection with FIGS. 7A and 7B.

Figure 10A:
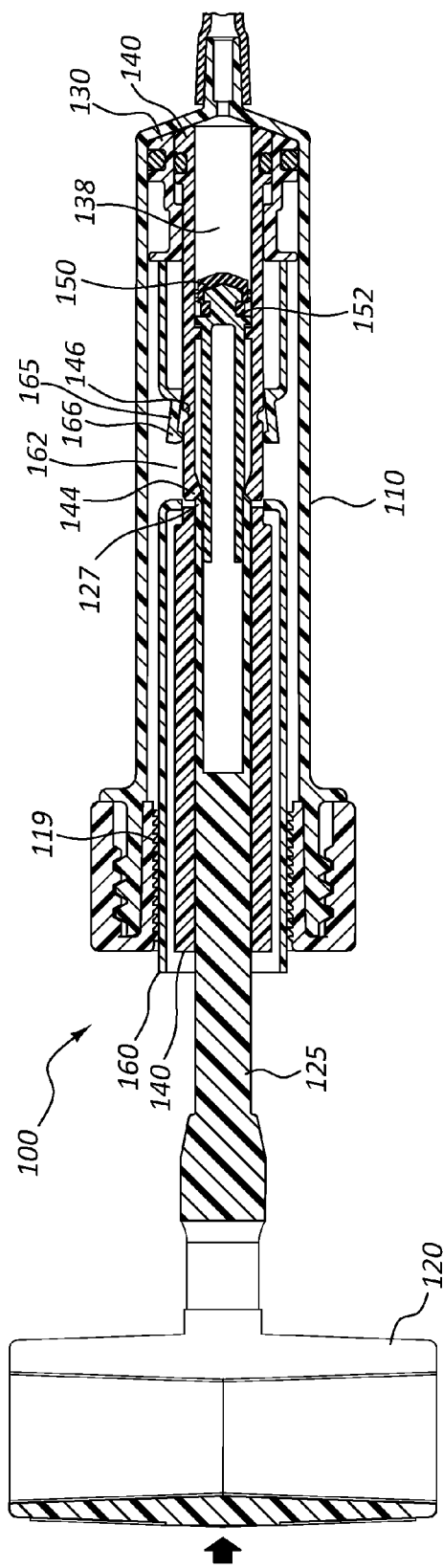
FIG. 10A is a first cross-sectional view of the inflation device of FIG. 1 in a third position.
Figure 10B:
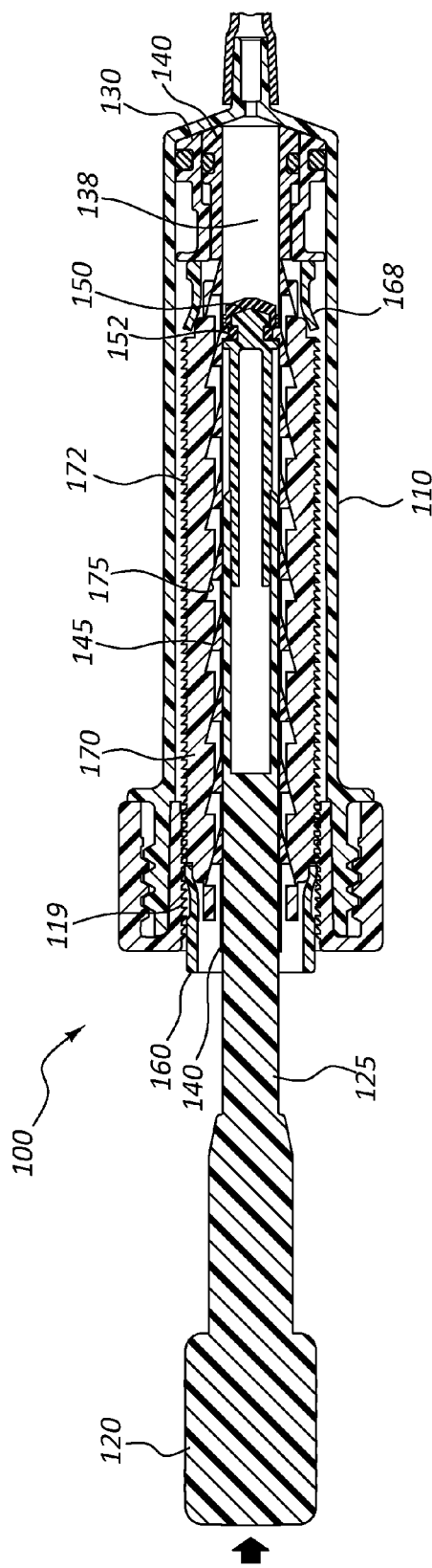
FIG. 10B is a second cross-sectional view of the inflation device of FIG. 10A.

As part of a therapy, a practitioner may fully advance the volume plunger (130, 140) and the inner plunger 150 in order to fully evacuate any existing fluid (such as air) from the inflation device 100. FIGS. 10A and 10B are cross-sectional views of the inflation device 100 of FIG. 1 in a third position. In the position of FIGS. 10A and 10B, the handle 120 has been advanced until the outer plunger 130 contacts the distal end of the syringe body 110. If the practitioner continues to displace the handle 120 after this contact, the reactionary force on the outer plunger 130 arrests the advancement of the outer plunger 130, but the force on the handle 120 may continue to advance the intermediate plunger 140 through the contact of the engagement arms 144 and the distal end of the plunger shaft 127. In this way, contact between the outer plunger 130 and the distal end of the syringe body 110 may exert a force configured to shift the inflation device 100 from the unlocked to the locked configuration. This response is analogous to the situation described above wherein pressure resistance on the outer plunger 130 precedes a shift to the locked position.

As shown in FIGS. 10A and 10B, the advancement of the inner plunger 140 with respect to the inner plunger 130 and locking sleeve 160 deflects the compliant nub arm 165 to deform outwardly (thus decoupling the intermediate plunger 140 and the locking sleeve 160 as the detent nub 166 becomes disengaged from the detent recess 146). In the position of FIGS. 10A and 10B, the windows 162 have moved into alignment with the engagement arms 144; thus, the engagement arms 144 are no longer constrained radially. Further advancement of the distal end of the plunger shaft 127 will thus force the engagement arms 144 radially outward. Further, the angled surfaces 145 of the intermediate plunger 140 and the angled surfaces 175 of the locking rails 170 cooperatively force the locking rails 170 radially outward as the locking sleeve 160 is displaced with respect to the intermediate plunger 140. Thus, the locking rail threads 172 engage the cap locking threads 119, coupling the thread rails 170, the locking sleeve 160, and the outer plunger 130 with respect to the syringe body 110. The biasing elements 168 are deflected radially outward as the locking rails 170 move radially outward.

In the position of FIGS. 10A and 10B, the volume plunger (130, 140) is disposed to fully evacuate the volume reservoir (114 of FIG. 9A), though the pressure reservoir 138 may still contain air. The physician may continue to advance the handle 120, which advances only the inner plunger 150 in this configuration, to evacuate the pressure reservoir 138 as well.

FIGS. 11A and 11B are cross-sectional views of the inflation device 100 of FIG. 1 in a fourth position, with the inner plunger 150 advanced to fully evacuate the pressure reservoir (138 of FIG. 10A). In other words, the inner plunger 150 may be advanced such that it fully evacuates the pressure reservoir (138 of FIG. 10A) when the inner plunger 150 is fully extended.

As compared to the position of FIGS. 10A and 10B, the engagement arms 144 are radially deflected by the distal end of the shaft 127, again as the windows 162 are in alignment with the engagement arms 144. The outer plunger 130, the intermediate plunger 140, the locking sleeve 160, the locking rails 170, the recess portion 146 and nub portions 166 of the detent, the angled surfaces of the intermediate plunger 145 and the angled surfaces of the locking rails 175, and the biasing elements 168 are in the same relative positions to each other as described in connection with FIGS. 10A and 10B.

Once the inflation device 100 is fully evacuated, the practitioner may draw back the volume plunger (130, 140) and the inner plunger 150 in order to fill the inflation device 100 with a desired fluid. Prior to retracting these components, the outlet of the syringe body 110 may be placed in fluid communication with a reservoir of a desired fluid, for example, saline, water, carbon dioxide, contrast fluid, and so forth.

FIGS. 12A and 12B are cross-sectional views of the inflation device 100 of FIG. 1 in a fifth position, with the volume plunger (130, 140) and the inner plunger 150 drawn back. As described above, in drawing back the handle 120, the practitioner may shift the inflation device 100 from the locked configuration to the unlocked configuration as follows. The practitioner may proximally displace the handle 120 (and thus the inner plunger 150) until the distal end of the shaft 127 moves proximally beyond the engagement arms 144. Once the distal end of the shaft 127 is no longer forcing the engagement arms 144 radially outward, the compliant engagement arms 144 may return radially inward, as the proximal end of the inner plunger 150 may have a smaller diameter than the distal end of the shaft 127. Interaction of the inner plunger seal 152 and the distal shoulder 148 of the intermediate plunger 140 may then cause proximal displacement of the handle 120 (and thus the inner plunger 150) to proximally displace the intermediate plunger 140 with respect to the locking sleeve 160, moving the engagement arms 144 out of alignment with the window 162, and reengaging the nub 166 and recess 146 detent portions. Further, the angled surfaces 145 of the intermediate plunger 140 move with respect to the angled surfaces 175 of the locking rails 170, allowing the biasing elements 168 to radially retract the locking rails 170 and disengaging the locking rails 170 and cap 118. The inflation device 100 is thus returned to the unlocked configuration, and further retraction of the handle 120 retracts both the volume plunger (130, 140) and the inner plunger 150.

The practitioner may then advance the handle 120 to displace fluid within the volume reservoir 114, for example to inflate an attached medical device. The practitioner may advance the handle 120 until the pressure within the volume reservoir 114 reaches a particular pressure. Of course, the pressure within the pressure reservoir 138, in fluid communication with the volume reservoir 114, is the same. FIGS. 13A and 13B are cross-sectional views of the inflation device 100 of FIG. 1 in a sixth position. In the position of FIGS. 13A and 13B the inflation device 100 is in the unlocked configuration and the volume plunger (130, 140) and inner plunger 150 have been advanced until the pressure within the volume reservoir 114 is at a pressure, designated $P_1$. The inflation device may be configured such that, at $P_1$, the pressure force acting on the outside plunger 130 is sufficient to shift the device to the locked configuration.

In other words, the pressure acting on the outside plunger 130 may cause the outside plunger 130 and the locking sleeve 160 to shift proximally as the intermediate plunger 140 continues to advance, deflecting the compliant nub arm 165 to deform outwardly (thus decoupling the intermediate plunger 140 and the locking sleeve 160 as the detent nub 166 becomes disengaged from the detent recess 146). This is analogous to the shift caused by the force exerted by the syringe body 110 on the outer plunger 130 as discussed in connection with FIGS. 10A and 10B. As with those figures, in FIGS. 13A and 13B, the windows 162 have moved into alignment with the engagement arms 144; thus, the engagement arms 144 are no longer constrained radially. Further advancement of the distal end of the plunger shaft 127 will thus force the engagement arms 144 radially outward. Further, the angled surfaces 145 of the intermediate plunger 140 and the angled surfaces 175 of the locking rails 170 cooperatively force the locking rails 170 radially outward as the locking sleeve 160 is displaced with respect to the intermediate plunger 140. Thus, the locking rail threads 172 engage the cap locking threads 119, coupling the thread rails 170, the locking sleeve 160, and the outer plunger 130 with respect to the syringe body 110. The biasing elements 168 are deflected radially outward as the locking rails 170 move radially outward.

At this point in the therapy, the medical device may be inflated, though not pressurized, and the locked configuration of the device may allow the practitioner to pressurize and depressurize the medical device quickly and easily as displacement of the handle 120 will only displace the inner plunger 150 within the pressure reservoir 138 (as long as the handle 120 is not pulled back such that the distal end of the handle 127 allows the engagement arms 144 to move radially inward).

FIGS. 14A and 14B are cross-sectional views of the inflation device 100 of FIG. 1 in a seventh position, with the device in a locked configuration. As described above, in this configuration, the practitioner may quickly pressurize and depressurize a medical device by displacing the handle 120.

For example, in vavuloplasty procedures, this may allow a practitioner to pressurize a balloon to a high pressure between heartbeats, with depressurizing during each heartbeat. As compared to the illustration of FIG. 13A, in FIGS. 14A and 14B, the inner plunger 150 has been advanced within the pressure reservoir 138; thus, the pressure reservoir 138 (and the volume reservoir 114 and any medical device in fluid communication therewith) is indicated at a second pressure, $P_2$. Because the inner plunger 150 is distally advanced as compared to the position of FIGS. 13A and 13B, $P_2$ is greater than $P_1$. The pressure measurements indicated in FIGS. 13A-15B assume the outlet of the inflation device 100 is in fluid communication with a medical device to be inflated.

FIGS. 15A and 15B are cross-sectional views of the inflation device 100 of FIG. 1 in an eighth position, with the device in the locked configuration and the inner plunger 150 drawn back as compared to the position of FIGS. 14A and 14B. Thus, the pressure shown in the volume 114 and pressure 138 reservoirs is shown as $P_3$. As the inner plunger 150 is drawn back, $P_3$ is smaller than $P_2$. This may be a position of the device between heartbeats, for example.

In FIGS. 14A-15B, the device remains in the locked configuration (as in FIGS. 13A and 13B), though the positions of the inner plunger 150 and handle 120 change between FIGS. 14A-14B and 15A-15B. Analogous to the discussion of FIGS. 11A and 11B as compared to the position of FIGS. 10A and 10B, in FIGS. 14A-15B, as compared to the position of FIGS. 13A and 13B, the engagement arms 144 are radially deflected by the distal end of the shaft 127. The outer plunger 130, the intermediate plunger 140, the locking sleeve 160, the locking rails 170, the recess portion 146 and nub portions 166 of the detent, the angled surfaces of the intermediate plunger 145 and the angled surfaces of the locking rails 175, and the biasing elements 168 are in the same relative positions to each other as described in connection with FIGS. 13A and 13B.

Various additional procedures may be performed using the techniques and device positions described in connection with FIGS. 8A-15B. It is within the scope of this disclosure to use any number of the positions or steps disclosed above (or intermediate positions between those shown) in any combination or order as part of a therapy. Further, though the inflation device of FIGS. 8A-15B is configured to automatically shift between the unlocked and locked configurations, in other embodiments the inflation device may be configured to be manually shifted from one configuration to another. For example, the inflation device may be configured such that rotation of the handle or actuation of a button or trigger shifts the device from one configuration to another. Additionally, while the device disclosed above has two configurations (and thus two combinations of plungers which are displaceable by the handle), in other embodiments an inflation device may comprise more plungers with more configurations. In some such embodiments, the device may be configured to incrementally shift configurations (and required input force) over a pressure range.

Figure 16:
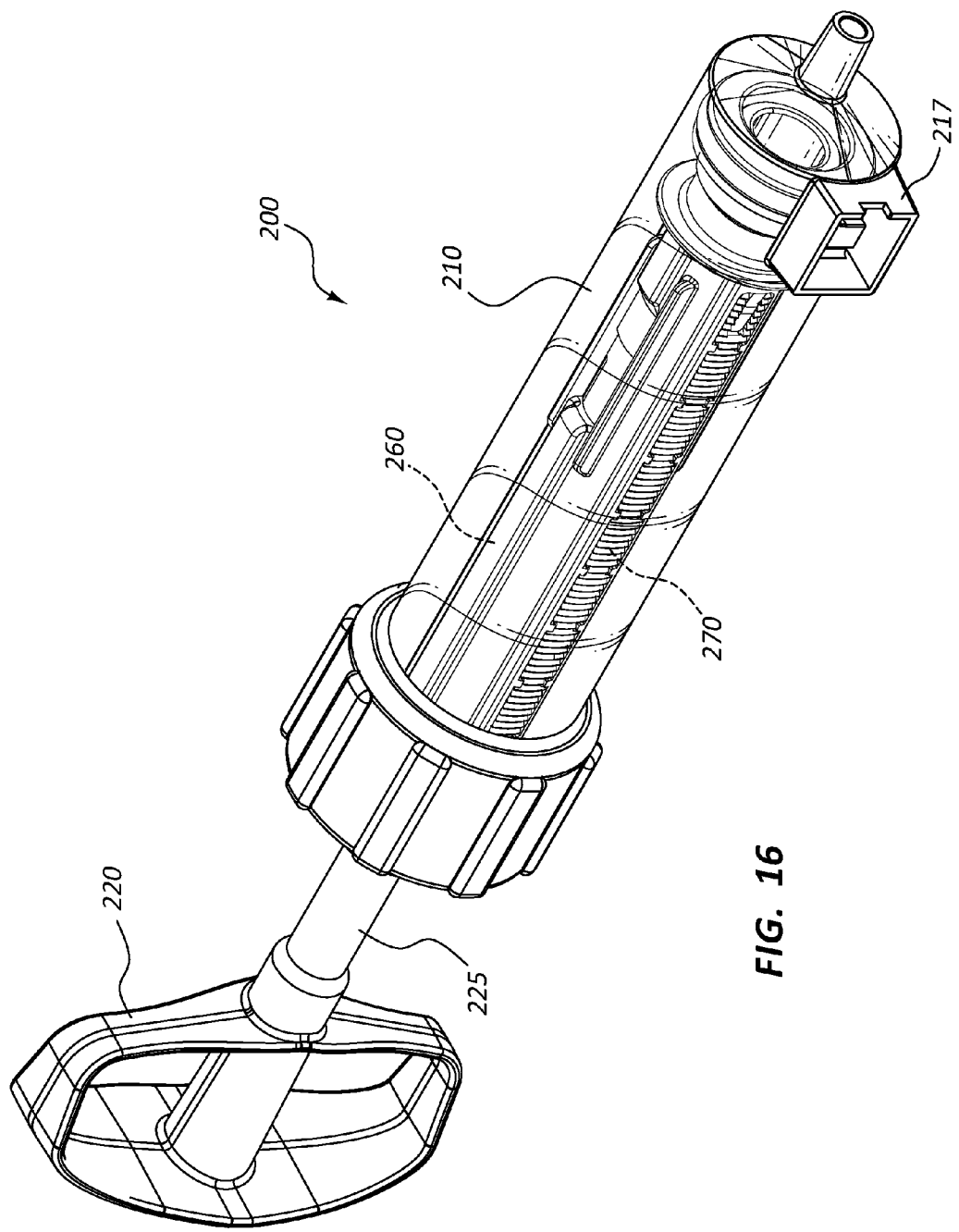
FIG. 16 is a front perspective view of another embodiment of an inflation device.

FIG. 16 is a front perspective view of another embodiment of an inflation device 200. The embodiment of FIG. 16 may include components that resemble components of FIGS. 1-15B in some respects. For example, the embodiment of FIG. 16 includes a syringe body 210 that may resemble the syringe body 110 of FIGS. 1-15B. It will be appreciated that all the illustrated embodiments have analogous features. Accordingly, like features are designated with like reference numerals, with the leading digits incremented to "2." Relevant disclosure set forth above regarding similarly identified features thus may not be repeated hereafter. Moreover, specific features of the inflation device and related components shown in FIG. 16 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the inflation device and related components of FIG. 16. Any suitable combination of the features, and variations of the same, described with respect to the inflation device and components illustrated in FIGS. 1-15B, can be employed with the inflation device and components of FIG. 16, and vice versa. This pattern of disclosure applies equally to further embodiments depicted in subsequent figures and described hereafter.

It will be appreciated by one of skill in the art having the benefit of this disclosure that the inflation device 200 of FIGS. 16-22 may function in an analogous manner to the inflation device 100 described in the preceding figures. Thus, while specific features and elements of the subsequent inflation device 200 will be described below, disclosure above regarding the relationship of components and the function of the inflation device 100 of the preceding figures may be applied to the device 200 of FIGS. 16-22.

The inflation device 200 of FIG. 16 comprises a body portion, syringe body 210 and a handle 220. As with the prior embodiment, a shaft 225 extends from the handle 220. Locking rails 270 and a locking sleeve 260, analogous to similarly indicated components in the prior embodiment, are also shown in FIG. 16. Additionally, the embodiment of FIG. 16 comprises a gauge mounting bracket 217 on the syringe body 210.

Figure 17:
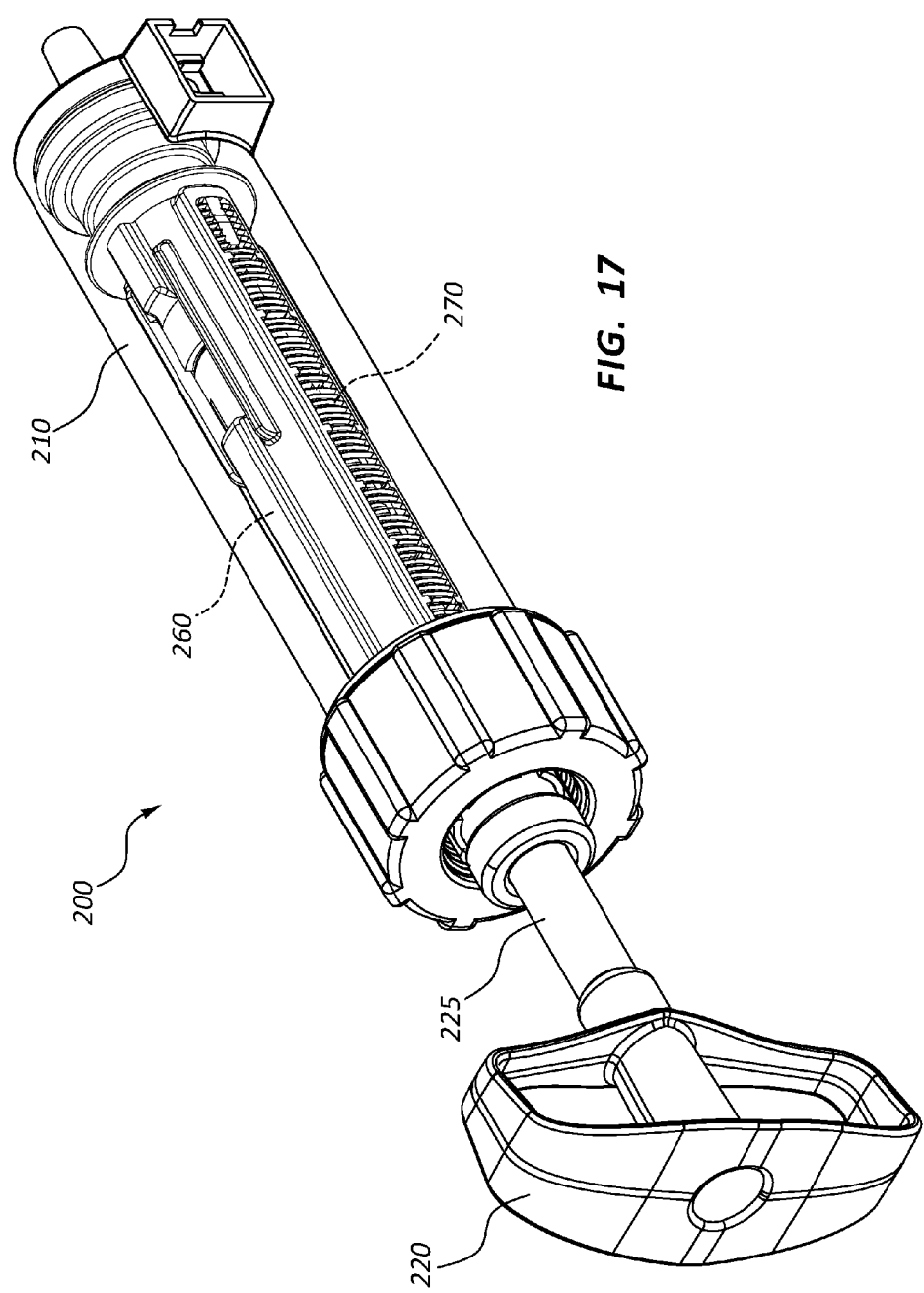
FIG. 17 is a rear perspective view of the inflation device of FIG. 16.

FIG. 17 is a rear perspective view of the inflation device 200 of FIG. 16. FIG. 17 illustrates the handle 220 and the shaft 225 of the inflation device 200 as well as the locking rails 270, locking sleeve 260, and syringe body 210 thereof.

Figure 18:
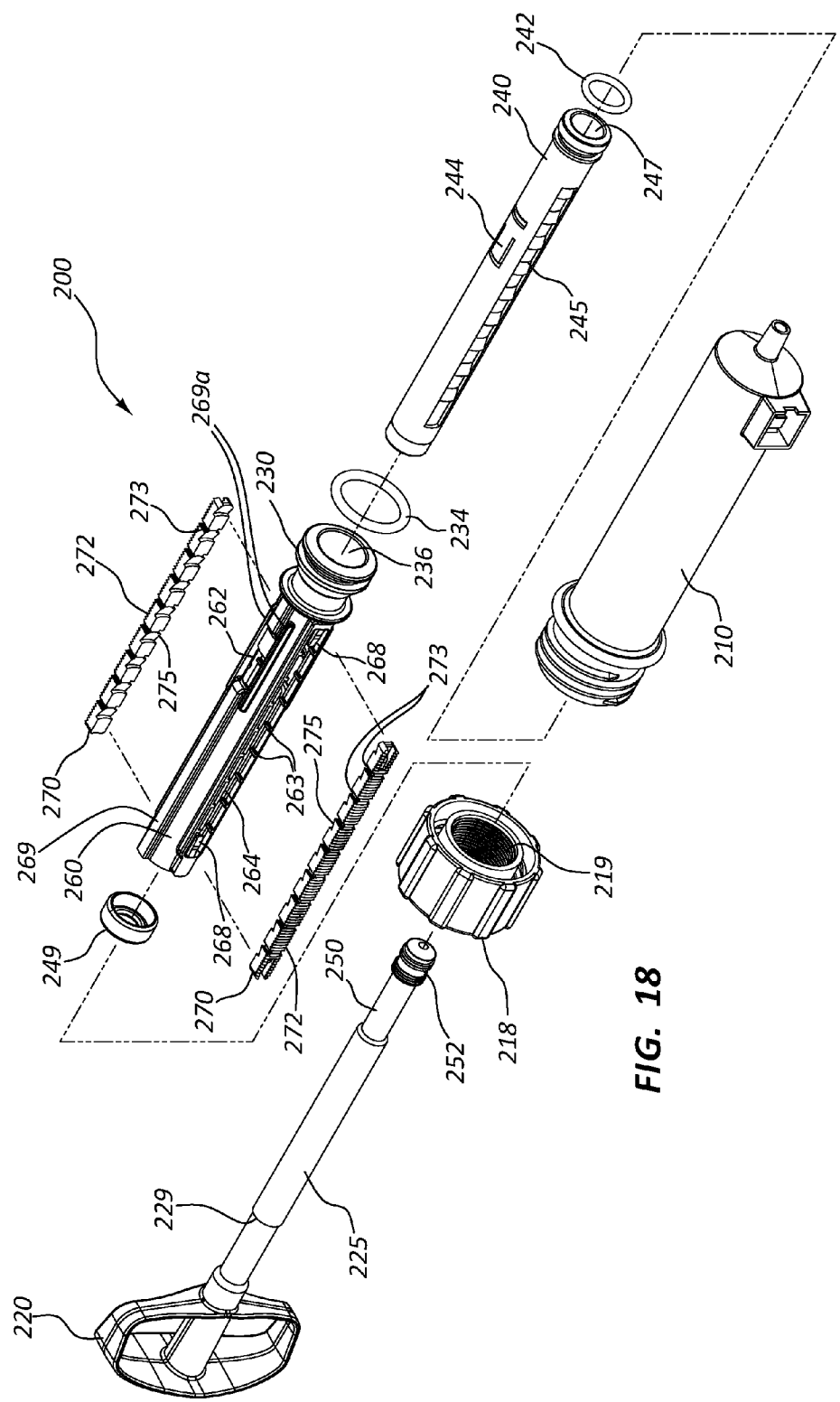
FIG. 18 is an exploded view of the inflation device of FIG. 16.

FIG. 18 is an exploded view of the inflation device 200 of FIG. 16. The exploded view of FIG. 18 illustrates the various components of the inflation device 200. Analogous to the previously described inflation device 100, the inflation device 200 of FIG. 18 comprises a syringe body 210 and cap 218 which may be configured with locking threads 219.

The inflation device 200 further comprises a handle 220 and shaft 225 which are integrally formed with an inner plunger 250 which is coupled to an inner plunger seal 252. This arrangement differs from the embodiment of FIGS. 1-15B in which the shaft 125 and inner plunger 150 were coupled, though not necessarily integrally formed. Similarly, in the embodiment of FIG. 18, a locking sleeve 260 is integrally formed with an outer plunger 230, components which were also not necessarily integral in the previously described embodiment.

An outer plunger seal 234 may be provided in connection with the outer plunger 230 which may further define an interior portion 236 of the outer plunger 230. An intermediate plunger 240 and an intermediate plunger seal 242 may be configured to be disposed within the interior portion 236 of the outer plunger 230. The intermediate plunger 240 may also define an interior portion 247, with the inner plunger 250 configured to be disposed therein.

As with the previous embodiment, the intermediate plunger 240 may comprise intermediate plunger angled surfaces 245 configured to function in connection with locking rail angled surfaces 275 provided on the locking rails 270. Further, as in the prior embodiment, the inflation device may be configured with engagement arms 244 disposed on the intermediate plunger 240 configured to function in connection with windows 262 in the locking sleeve 260.

The locking rails 270 may comprise locking rail threads 272 configured to engage the cap locking threads 219 of the cap 218. The locking sleeve 260 may comprise slots 264 configured to receive the locking rails 270. Mating grooves 273 and ridges 263 on these components may be disposed such that movement of the locking rails 270 with respect to the locking sleeve 260 is constrained. Further, biasing elements 268 may be coupled to the locking sleeve 270 and configured to interact with the locking rails 270, analogous to the components described in the prior embodiment.

The locking sleeve 260 may also include a guide groove configured to mate with a guide rail formed on the intermediate plunger 240, such as, for example, similar to the guide rail 149 and guide groove 169 in the embodiment of FIGS. 1-15B.

The locking sleeve 260 may also comprise ribs 269a formed on either side of the window 262. The ribs 269a may serve to add structural stiffness to the locking sleeve 260 and prevent outward bowing of the locking sleeve 260 under pressure.

Finally, the inflation device may comprise an intermediate plunger cap 249 configured to be coupled to the proximal end of the intermediate plunger 240 when the inflation device 200 is assembled. The intermediate plunger cap 249 may be configured to contact a shaft shoulder 229 on the shaft 225 when the handle 220 is retracted proximally. Contact between the shaft shoulder 229 and the intermediate plunger cap 249 may be configured to likewise draw back the intermediate plunger 240 when the shaft shoulder 229 and intermediate plunger cap 249 are in contact with each other.

FIG. 19 is a top view of the inflation device 200 of FIG. 16, and FIG. 20 is a front view of the inflation device 200 of FIG. 16. FIGS. 19 and 20 illustrate the handle 220, shaft 225, syringe body 210, outer plunger 230, locking sleeve 260, and locking rails 270 of the inflation device 200. Additionally, cross-sectional planes for FIGS. 21 and 22 are illustrated in these figures.

FIG. 21 is a cross-sectional view of the inflation device 200 of FIG. 19, taken through plane 21-21. The handle 220, shaft 225, syringe body 210, outer plunger 230, intermediate plunger 240, inner plunger 250, and locking sleeve 260 are shown in this figure. These elements interact and function analogously to the similarly designated elements of the preceding embodiment. For example, a window 262 is provided in the locking sleeve 260, in connection with engagement arms 244 of the intermediate plunger 240. Furthermore, in some embodiments, the distal end of the engagement arms 244 may comprise a slight angle, to mitigate binding of the mechanism when the engagement arms 244 expand and retract radially through the windows 262.

Further, as with the preceding embodiment, the locking sleeve 260 and intermediate plunger 240 are releasably coupled to each other in the unlocked configuration by a detent 266, 246. More specifically, a recess portion 246 and a nub portion 266 of a detent couple the locking sleeve 260 and the intermediate plunger 240. The nub portion 266 of the detent may be positioned on a compliant nub arm 265 configured to deform outwardly (thus decoupling the intermediate plunger 240 and the locking sleeve 260) in response to a force or forces on these components as further detailed above. In the unlocked configuration, however, the nub arm 265 maintains the position of the nub portion 266 within the recess portion 246.

In any of the embodiments described herein, the properties of the nub arm 265 may be configured to control the force at which the detent 266, 246 disengages. As described above, this disengagement may be due to pressure within the syringe body 210. Thus, the properties of the nub arm 265 may be configured to control the pressure at which the inflation device 200 shifts configurations. The nub arm 265 may be a cantilevered component coupled to the locking sleeve 260 only at its base. Thus, the length, the thickness, and the material properties of the nub arm 265 may each impact the force required to disengage the detent 266, 246. In some embodiments, this may be adjustable by a user. For example, the nub arm 265 may be configured with a ring disposed around a circumference of the locking sleeve 260, the ring configured to be disposed about the nub arm 265. Moving the ring distally may be configured to lengthen the effective length of the nub arm 265 (adjusting the effective length of the cantilever), while moving the ring proximally would shorten the effective length thereof. Thus, the effective length of the nub arm 265, and thus the force at which the detents 266, 246 disengage, may be adjustable by a user. The ring may be displaced by rotating the ring on threads, for instance.

Similarly, the nub arm 265 and associated components 266, 246 may be disposed at an alternate location on the inflation device 200 to allow a user to adjust the nub arm 265 without disassembling the inflation device 200. For example, nub arm 265 and associated detent 266, 246 may be posited near the proximal end of the locking sleeve 260 and intermediate plunger 240. This may allow a user to twist a ring disposed adjacent the intermediate plunger cap 249, for example.

FIG. 22 is a cross-sectional view of the inflation device of FIG. 20, taken through plane 22-22. The handle 220, shaft 225, syringe body 210, outer plunger 230, intermediate plunger 240, inner plunger 250, and locking sleeve 260 are shown in this figure. The locking rails 270 are also shown, along with the locking rail angled surfaces 275, the intermediate plunger angled surfaces 245, the locking sleeve threads 272, and the cap threads 219. Further, the intermediate plunger cap 249 as well as the shaft shoulder 229 are illustrated. This cross-sectional view illustrates how the shaft shoulder 229 and intermediate plunger cap 249 may interact to pull the intermediate plunger 240 proximally when the handle 220 is displaced proximally and the shaft shoulder 229 is in contact with the intermediate plunger cap 249.

Figure 23:
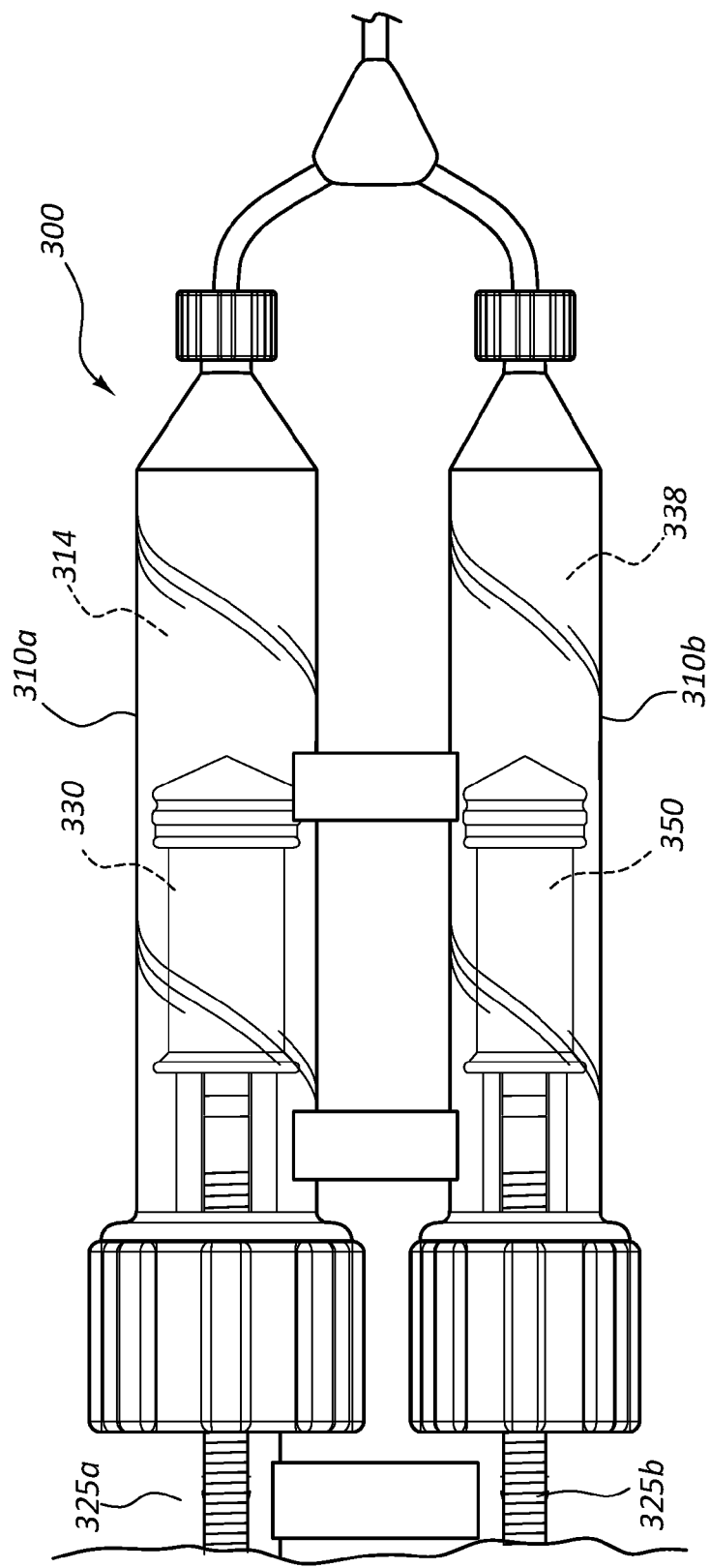
FIG. 23 is a top view of another embodiment of an inflation device.
Figure 24A:
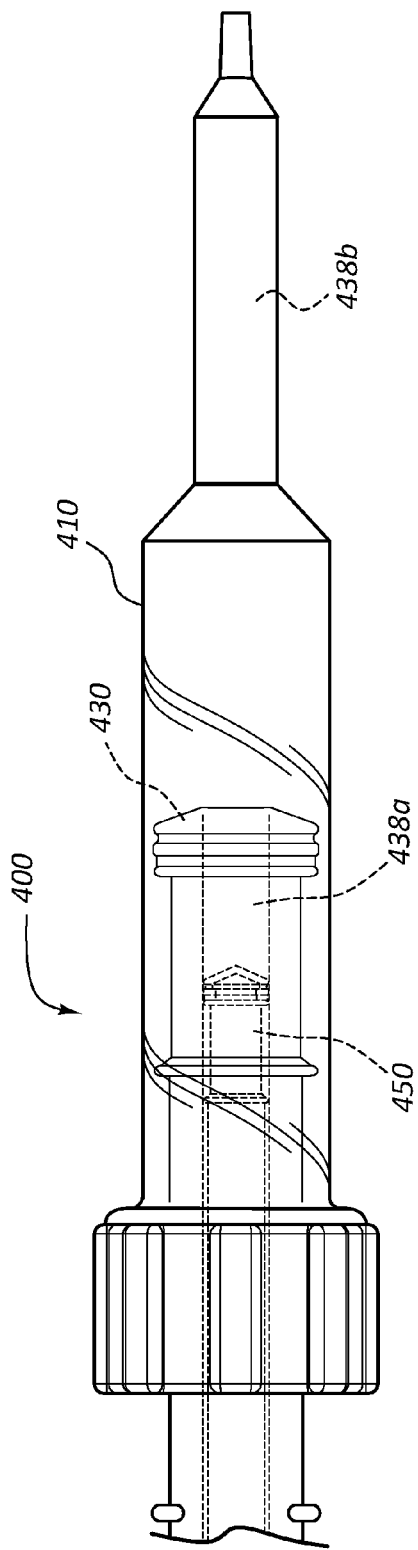
FIG. 24A is a top view of another embodiment of an inflation device in a first position.
Figure 24B:
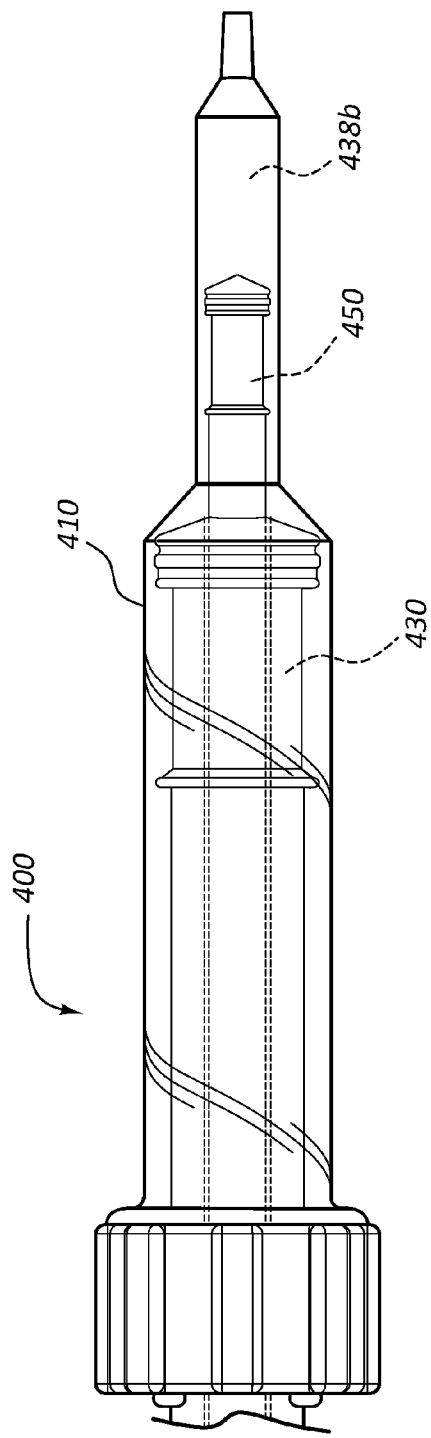
FIG. 24B is a top view of the inflation device of FIG. 24A in a second position.
Figure 25:
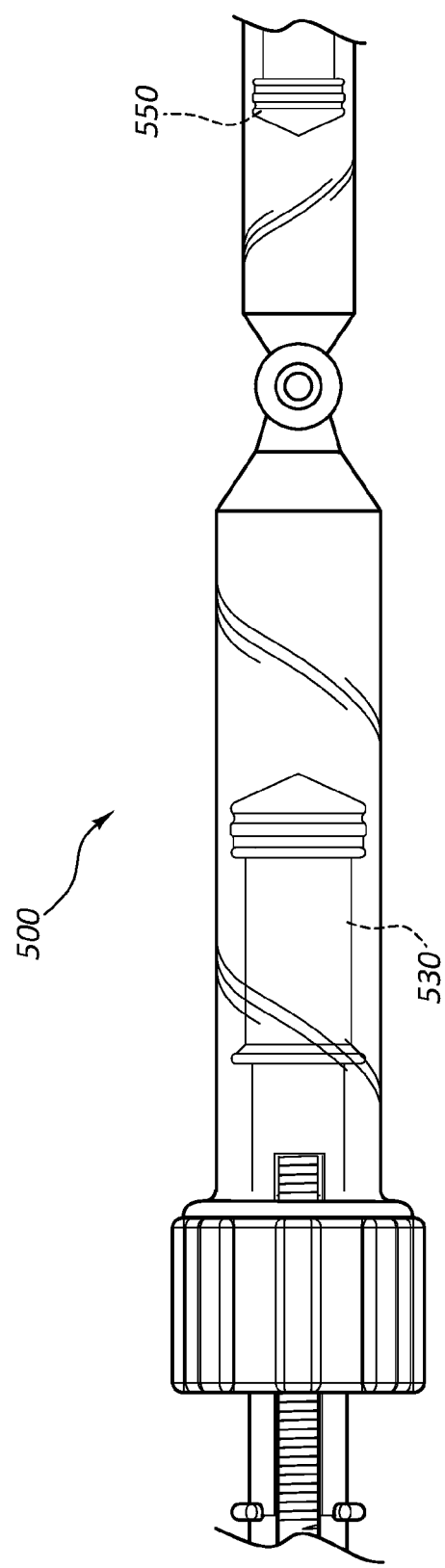
FIG. 25 is a top view of another embodiment of an inflation device.

FIGS. 23-25 illustrate additional embodiments of inflation devices having multiple plungers of differing effective areas. Any inflation device utilizing plungers of differing effective areas is within the scope of this disclosure, regardless of the particular geometry or alignment of any such devices.

FIG. 23 is a top view of another embodiment of an inflation device 300. In the illustrated embodiment, the inflation device 300 comprises a first syringe body 310a and a second syringe body 310b with a first plunger 330 disposed within the first syringe body 310a and a second plunger 350 disposed within the second syringe body 310b. The first syringe body 310a and the first plunger 330 have larger diameters than the second syringe body 310b and the second plunger 350. The fluid reservoirs 314 and 338, associated with syringe bodies 310a and 310b respectively, are connected such that both are in fluid communication with each other and any connected medical device. The plungers 330, 350 may also be coupled to first 325*a* and second 325*b* handle shafts, respectively.

To facilitate the displacement of fluid using the inflation device 300, the practitioner may advance and lock in place the first plunger 330 then subsequently advance the second plunger 350. As the second plunger 350 has a smaller effective surface area, it may be easier to advance the second plunger 350 (as compared to the first plunger 330) under high pressure. The first plunger 330 may be locked in place manually or automatically, analogous to any of the mechanisms discussed in any embodiment here. In some instances, the first plunger 330 may be manually locked in place by rotating the first handle shaft 325*a*. Thus, the practitioner may displace fluid by advancing the first plunger 330 a shorter distance within the first syringe body 310*a* than that which would have been needed to displace an equal volume of fluid using only the second plunger 350 in the second syringe body 310*b*. Again, the decreased effective surface area of the second plunger 350 with respect to the first plunger 330 may allow the practitioner to continue increasing the fluid pressure without needing to apply a force with as large a magnitude as that which would have been needed to displace fluid using the first plunger 330 alone. This process may also permit the practitioner to displace fluid more quickly than by attempting to advance either plunger alone.

FIG. 24A is a top view of another embodiment of an inflation device 400 in a first position, while FIG. 24B is a top view of the inflation device 400 of FIG. 24A in a second position. In this embodiment, a first 430 and second 450 plunger may each independently travel within a single contiguous syringe body 410. In the illustrated embodiment, the two plungers 430, 450 have different effective surface areas, with the first plunger 430 having a greater effective surface area than the second plunger 450. In the illustrated configuration, where the plungers 430, 450 travel within the syringe body 410, a practitioner may advance the first plunger 430 to displace a first volume of fluid under relatively low pressure. When the first plunger 430 has been advanced (perhaps, though not necessarily, to the distal end of the syringe body 410), the second plunger 450 may be advanced to displace a second volume of fluid under higher pressure. In the illustrated embodiment, the second plunger 450 is configured to travel along a pressure reservoir 438*a*, 438*b* partially comprised of an interior portion of the first plunger 450, portion 438*a*, and partially comprised of an interior portion of the syringe body 410, portion 438*b*. Disposing of a portion of the pressure reservoir 438*a*, 438*b* partially within the first plunger 430 may be configured to create a longer travel path for the second plunger 450, without increasing the overall length of the syringe body 410.

In other inflation devices (for example, the inflation device 500 shown in FIG. 25), the plungers need not be positioned parallel to each other. FIG. 25 illustrates the inflation device 500 in which two plungers 530, 550 are oppositely oriented such that displacement of each plunger 530, 550 toward the other plunger displaces fluid within the inflation device 500.

Figure 26:
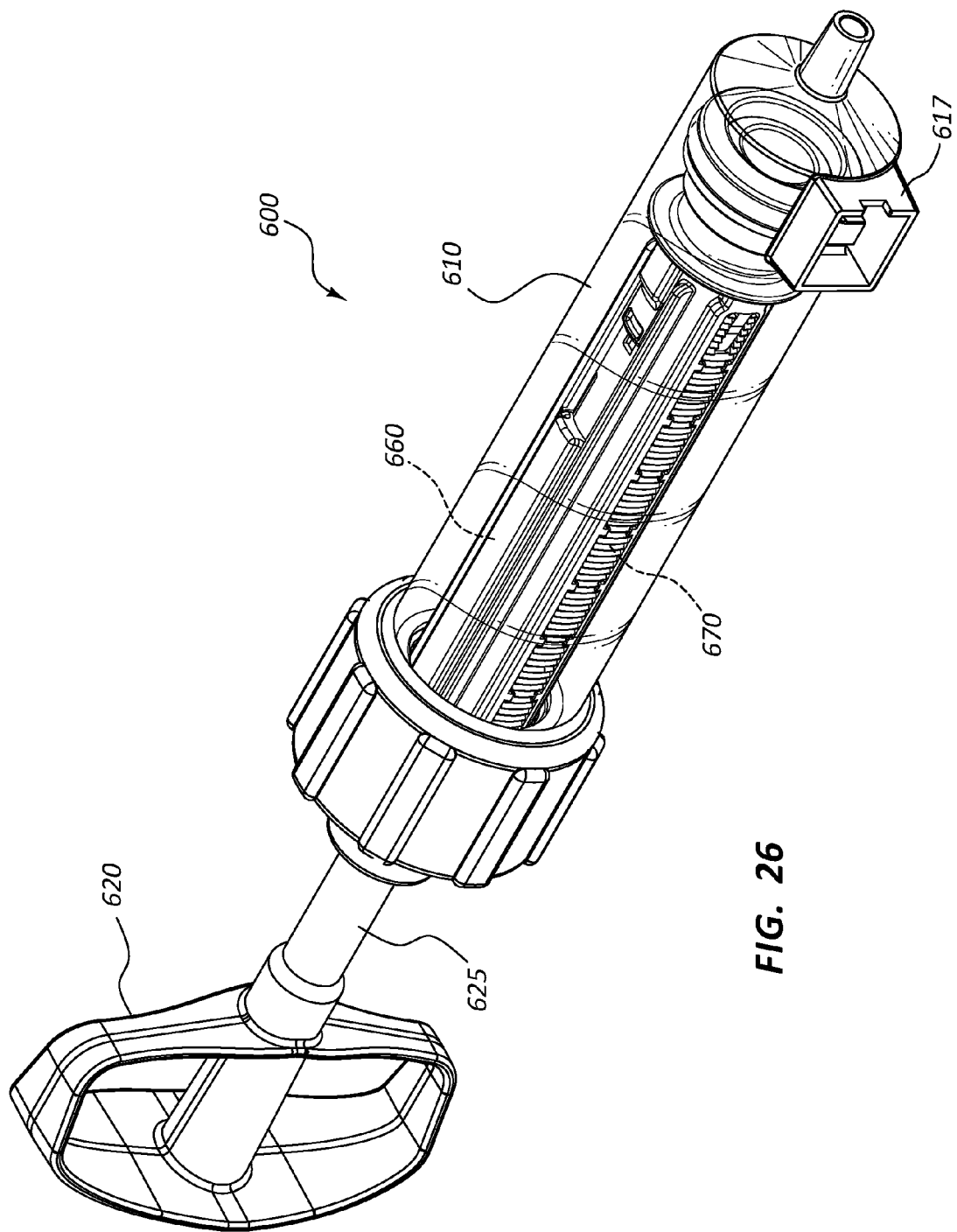
FIG. 26 is a front perspective view of another embodiment of an inflation device.

FIG. 26 is a front perspective view of another embodiment of an inflation device 600. The embodiment of FIG. 26 may include components that resemble components of FIGS. 1-15B and 16-22 in some respects. For example, the embodiment of FIG. 26 includes a syringe body 610 that may resemble the syringe body 110 of FIGS. 1-15B and the syringe body 210 of FIGS. 16-22. It will be appreciated that all the illustrated embodiments have analogous features. Accordingly, like features are designated with like reference numerals, with the leading digits incremented to "6." Relevant disclosure set forth above regarding similarly identified features thus may not be repeated hereafter. Moreover, specific features of the inflation device and related components shown in FIG. 26 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the inflation device and related components of FIG. 26. Any suitable combination of the features, and variations of the same, described with respect to the inflation device and components illustrated in FIGS. 1-15B and FIGS. 16-22, can be employed with the inflation device and components of FIG. 26, and vice versa. This pattern of disclosure applies equally to further embodiments depicted in subsequent figures and described hereafter.

It will be appreciated by one of skill in the art having the benefit of this disclosure that the inflation device 600 of FIGS. 26-38 may function in an analogous manner to the inflation device 100 and inflation device 200 described in the preceding figures. Thus, while specific features and elements of the subsequent inflation device 600 will be described below, disclosure above regarding the relationship of components and the function of the inflation device 100 and inflation device 200 of the preceding figures may be applied to the device 600 of FIGS. 26-38.

The inflation device 600 of FIG. 26 comprises a body portion, syringe body 610 and a handle 620. As with the prior embodiments, a shaft 625 extends from the handle 620. Locking rails 670 and a locking sleeve 660, analogous to similarly indicated components in the prior embodiments, are also shown in FIG. 26. Additionally, the embodiment of FIG. 26 comprises a gauge mounting bracket 617 on the syringe body 610.

Figure 27:
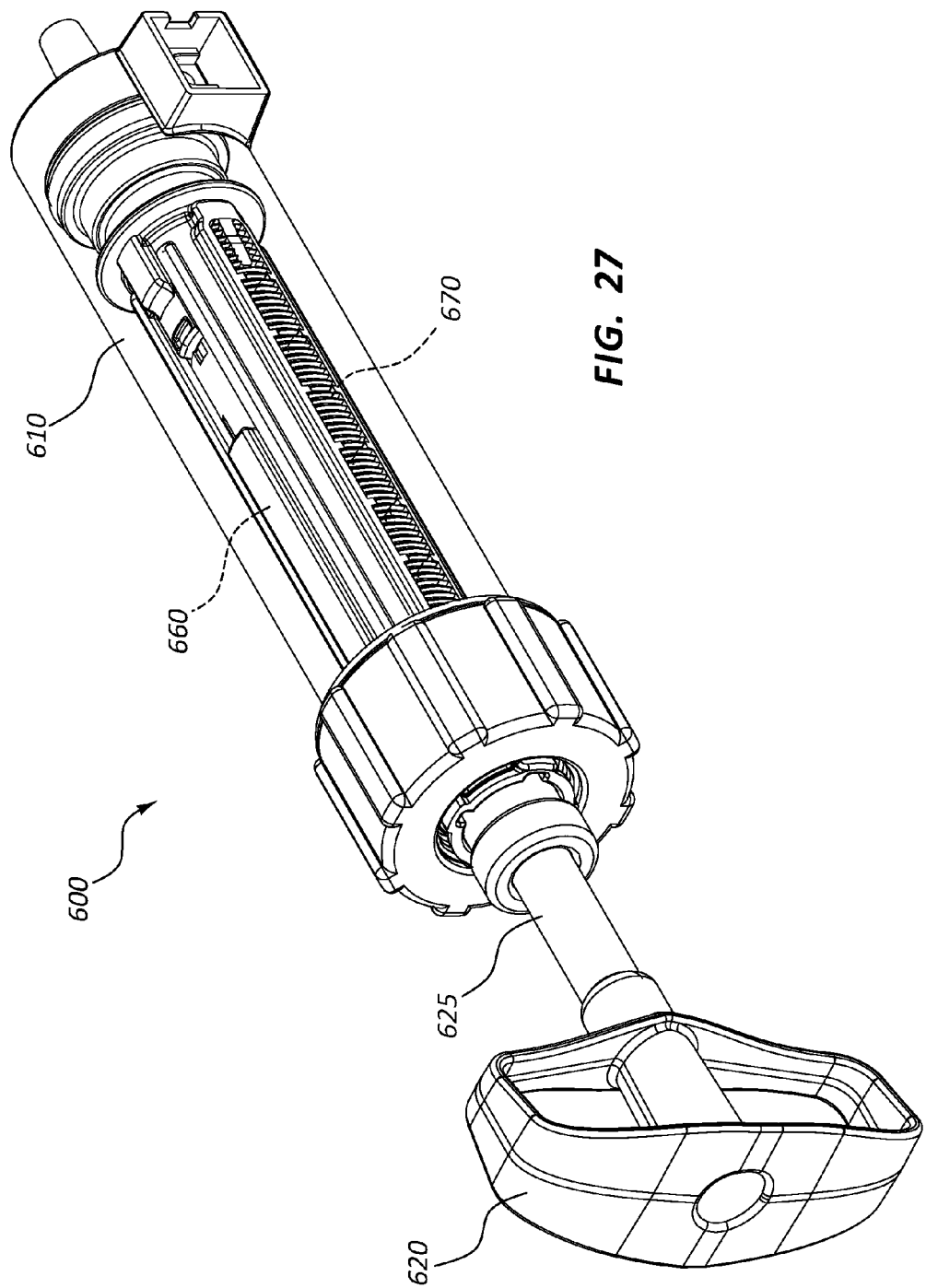
FIG. 27 is a rear perspective view of the inflation device of FIG. 26.

FIG. 27 is a rear perspective view of the inflation device 600 of FIG. 26. FIG. 27 illustrates the handle 620 and the shaft 625 of the inflation device 600 as well as the locking rails 670, locking sleeve 660, and syringe body 610 thereof.

Figure 28:
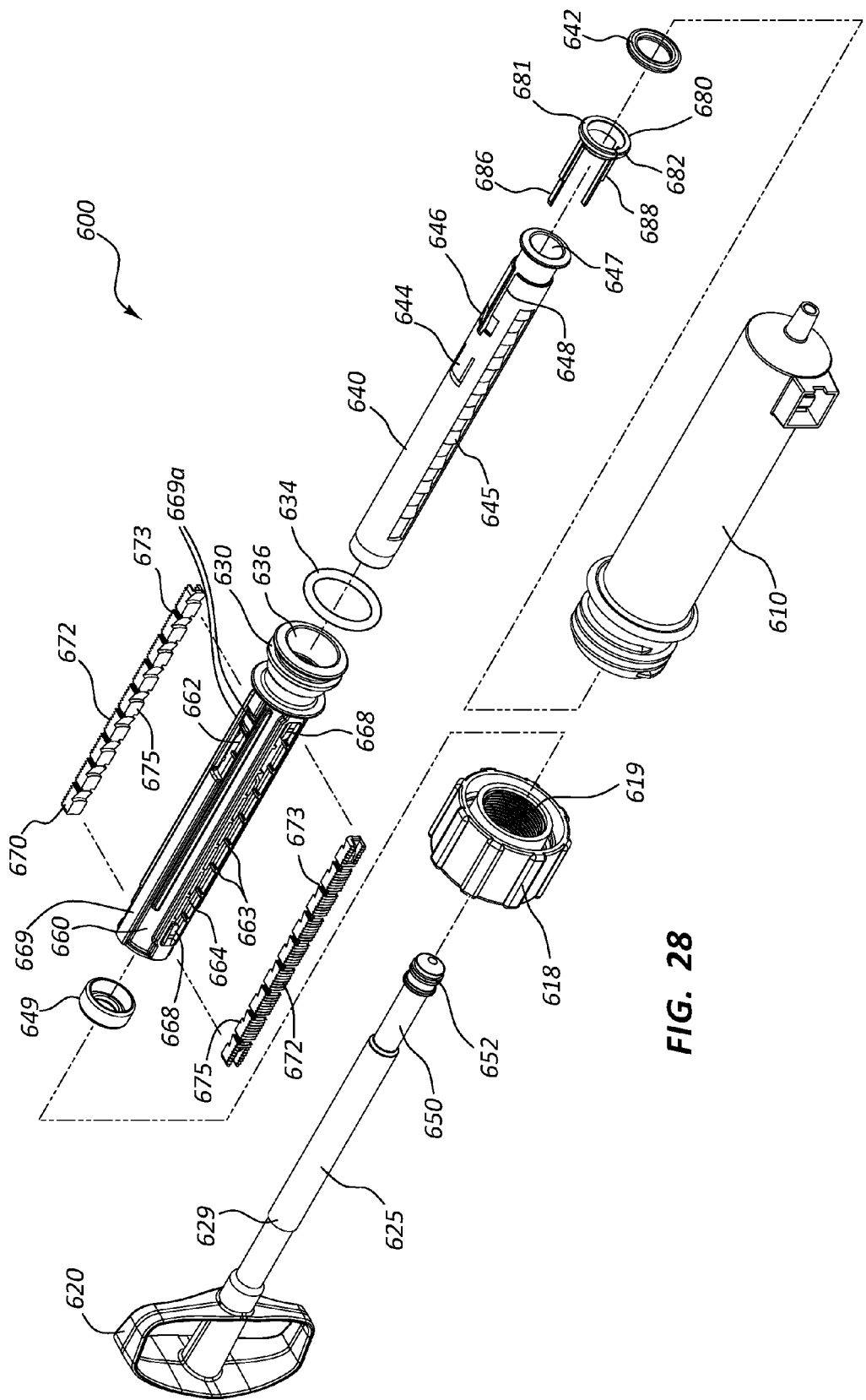
FIG. 28 is an exploded view of the inflation device of FIG. 26.

FIG. 28 is an exploded view of the inflation device 600 of FIG. 26. The exploded view of FIG. 28 illustrates the various components of the inflation device 600. Analogous to the previously described inflation device 100 and inflation device 200, the inflation device 600 of FIG. 28 comprises a syringe body 610 and cap 618 which may be configured with locking threads 619.

The inflation device 600 further comprises a handle 620 coupled to the shaft 625. In the illustrated embodiment, the shaft 625 is integrally formed with an inner plunger 650 and an inner plunger seal 652. This arrangement differs from the embodiment of FIGS. 1-15B in which the shaft 125 and inner plunger 150 were coupled, though not necessarily integrally formed. This arrangement also differs from the embodiment of FIGS. 16-22 in which the handle 620 and the shaft 625 were integrally formed. It should be understood that the present disclosure encompasses integrally and non-integrally formed variations of the illustrated embodiments.

Similar to the embodiment of FIG. 18, a locking sleeve 660 is integrally formed with an outer plunger 630. The locking sleeve 660 may include a guide groove configured to mate with a guide rail formed on the intermediate plunger 640, such as, for example, similar to the guide rail 149 and guide groove 169 in the embodiment of FIGS. 1-15B. The locking sleeve 660 may also comprise ribs 669a formed on either side of the window 662. The ribs 669a may serve to add structural stiffness to the locking sleeve 660 and prevent outward bowing of the locking sleeve 660 under pressure.

The inflation device 600, like the inflation device 100 and the inflation device 200 may be configured to achieve a maximum pressure of 6-12 ATM or more.

An outer plunger seal 634 may be provided in connection with the outer plunger 630 which may further define an interior portion 636 of the outer plunger 630. An intermediate plunger 640, slidable prong 680, and an intermediate plunger seal 642 may be configured to be disposed within the interior portion 636 of the outer plunger 630. The intermediate plunger 640 may also define an interior portion 647, with the inner plunger 650 configured to be disposed therein.

The slidable prong 680 may comprise a ring 681 configured for surrounding the recessed ring 641 of the intermediate plunger 640. The slidable prong 680 may comprise a gap 682. The gap 682 may allow for temporary oval flexing of the ring 681 during assembly of the inflation device 600. The two prong arms 688 may extend proximally away from the ring 681. The prong arms 688 may be configured to mate with the corresponding channel 648 formed in the outer surface of intermediate plunger 640. Each of the prong arms 688 may comprise a prong tip 686 that may have a thickness less than the thickness of the remainder of the prong arm 688.

Regarding the outer surface of intermediate plunger 640, each of the two channels 648 may have the same depth as the recessed ring 641. The deepest portion of the recessed portions 646 may be the same as the depth of the channels 648. The channels 648 may extend proximally beyond the recessed portions 646. Each recess portion 646 may be circumferentially wider (meaning the width around the perimeter of the outer surface of the intermediate plunger 640) than the width of the corresponding channel 648. Therefore, the entire proximal edge of the clip tip 666 may engage the proximal edge of the recess portion 646, except for that portion of the proximal edge of the clip tip 666 that lies in the channel 648. The recessed ring 641 is longitudinally wide enough (meaning the width along the longitudinal axis of the intermediate plunger 640) to receive the ring 681 of the slidable prong 680 and also the seal 642. The recessed ring 641 is also longitudinally wide enough to allow travel of the ring 681 and the seal 642, both proximally and distally, along the bottom surface of the recessed ring 641. Each channel 648 is configured to allow a prong arm 688 to slide proximally and distally along the length of the channel 648. The purpose of the slidability of the prong arms 688 will be discussed in more detail below.

As with inflation device 100 and inflation device 200, the intermediate plunger 640 may comprise intermediate plunger angled surfaces 645 configured to function in connection with locking rail angled surfaces 675 provided on the locking rails 670. Further, as in inflation device 100 and inflation device 200, the inflation device 600 may be configured with engagement arms 644 disposed on the intermediate plunger 640 configured to function in connection with windows 662 in the locking sleeve 660.

The locking rails 670 may comprise locking rail threads 672 configured to engage the cap locking threads 619 of the cap 618. The locking sleeve 660 may comprise slots 664 configured to receive the locking rails 670. Mating grooves 673 and ridges 663 on these components may be disposed such that movement of the locking rails 670 with respect to the locking sleeve 660 is constrained. Further, biasing elements 668 may be coupled to the locking sleeve 670 and configured to interact with the locking rails 670, analogous to the components described in inflation device 100 and inflation device 200.

Finally, the inflation device 600 may comprise an intermediate plunger cap 649 configured to be coupled to the proximal end of the intermediate plunger 640 when the inflation device 600 is assembled. The intermediate plunger cap 649 may be configured to contact a shaft shoulder 629 on the shaft 625 when the handle 620 is retracted proximally. Contact between the shaft shoulder 629 and the intermediate plunger cap 649 may be configured to likewise draw back the intermediate plunger 640 when the shaft shoulder 629 and intermediate plunger cap 649 are in contact with each other.

FIG. 29 is a top view of the inflation device 600 of FIG. 26, and FIG. 30 is a side view of the inflation device 600 of FIG. 26. FIGS. 29 and 30 illustrate the handle 620, shaft 625, syringe body 610, outer plunger 630, locking sleeve 660, and locking rails 670 of the inflation device 600. Additionally, cross-sectional planes for FIGS. 31 and 32 are illustrated in these figures.

FIG. 31 is a cross-sectional view of the inflation device 600 of FIG. 29, taken through plane 31-31. The handle 620, shaft 625, syringe body 610, outer plunger 630, intermediate plunger 640, inner plunger 650, and locking sleeve 660 are shown in this figure. These elements interact and function analogously to the similarly designated elements of inflation device 100 and inflation device 200. For example, a window 662 is provided in the locking sleeve 660, in connection with engagement arms 644 of the intermediate plunger 640. Furthermore, in some embodiments, the distal end of the engagement arms 644 may comprise a slight angle, to mitigate binding of the mechanism when the engagement arms 644 expand and retract radially through the windows 662.

Further, as with inflation device 100 and inflation device 200, the locking sleeve 660 and intermediate plunger 640 are releasably coupled to each other in the unlocked configuration by a detent 666, 646. More specifically, a recess portion 646 and a clip tip 666 of a detent couple the locking sleeve 660 and the intermediate plunger 640. The clip tip 666 of the detent may be positioned on a compliant clip arm 665 configured to deform and maintain engagement with the recess portion 646 until the clip tip portion 666 is pushed outwardly (thus decoupling the intermediate plunger 640 and the locking sleeve 660) by proximal movement of the prong tip 686 along the channel 646. In the unlocked configuration, however, the clip arm 665 maintains the position of the clip tip 666 within the recess portion 646.

Unlike with the nub portion 166 and 266, the clip tip 666 may be configured to deform in the distal direction and still maintain engagement with the recess portion 646. Each clip arm 665 may comprise a notch 666' formed in the outer surface of the clip tip 666. The notch 666' reduces the mass of the material adjacent the clip tip 666 and allows for movement of the clip tip 666 relative to the remainder of the clip arm 665.

Similar to inflation device 100 and inflation device 200, the clip arms 665 are radially inset from the remainder of the syringe body 610. In the embodiment of the inflation device 600 the clip arms 665 are radially inset by a sigmoid curve-shaped bend. As illustrated in FIG. 31, across the width of each channel 648, the inner surface of the corresponding clip arm 665 may be separated from the outer surface of the intermediate plunger 640 by the corresponding prong tip 686. Other than across the width of the channel 648, the inner surface of the clip arm 665 may lay upon the outer surface of the intermediate plunger 640. Each prong tip 686 may be longer than the corresponding inner surface of the clip arm 665.

Turning now to operation of the slidable prong 680, the slidable prong 680 may be configured to switch the inflation device 600 from the "unlocked configuration" to the "locked configuration." When the slidable prong 680 is in the distal position, as illustrated in FIG. 31, then the clip tips 666 may engage with recess portions 646. In contrast, as the slidable prong 680 moves proximal, the prong tips 686 slide underneath the respective clip tip 666. This pushes outward the proximal edge of each clip tip 666 and disengages it from the corresponding recess portion 646. Upon disengagement, the intermediate plunger 640 may be able to move distally relative to the outer plunger 630 and bring engagement arms 644 into alignment with the windows 662 and move locking rails 670 outward into the locked configuration, similar as discussed with analogous elements of inflation device 100 and inflation device 200.

The seal 642 may be configured to control movement of the slidable prong 680 in the proximal direction. In an unpressurized state, the seal 642 and the ring 681 of the slidable prong 680 may be located distally in recessed ring 641, as illustrated in FIG. 31. As pressure increases inside the syringe body 610, small volumes of pressurized fluid may pass between outer plunger 630 and intermediate plunger 640 and pressurize seal 642. The seal 642 may be an X-shaped elastomeric ring, such as a Quad-Ring®. As the pressure builds (such as by distal advancement of the plungers 630, 640, and 650) the seal 642 may begin to slide proximal and push slidable prong 680 in the proximal direction. At a given pressure, such as at about 2-3 ATM, then the seal may move the slidable prong 680 proximal enough to disengage the detent 666,646.

Each detent 666,646 may be reengaged by retraction of the intermediate plunger 640. The proximal lip of the slidable prong 680 may be configured to engage with an inner surface of the outer plunger 630. Also, each of the prong arms 688, where the thickness reduces to that of the prong tips 686, may be configured to engage with the corresponding inner surface of the sigmoid curve of the clip arms 665. As the intermediate plunger 640 is retracted and the slidable prong 680 engages with the inner surfaces of the clip arms 665 and the outer plunger 630, the slidable prong 680 and the seal 642 (by virtue of location next to the slidable prong 680) are moved to the distal end of the recessed ring 641. It should be understood by reference to FIG. 31 that when the intermediate plunger 640 is retracted sufficient to move the slidable prong 680 and the seal 642 to the distal end of the recessed ring 641, then the proximal edge of the recess portions 646 may be proximally-spaced away from the proximal edge of the clip tips 666. As the intermediate plunger 640 is slightly distally advanced, the slidable prong 680 and the seal 642 may stay at the distal end of the recessed ring 641. Meanwhile, the proximal edge of the clip tips 666 may reengage with the proximal edge of the recess portion 646, placing the components of the inflation device 600 back in the position illustrated in FIG. 31.

It should be understood that the elements of the inflation device 600 not specifically discussed that are analogous to the elements of the inflation device 100 and the inflation device 200, "lock" and "unlock" in a similar fashion.

It should be understood that any of the elements of any of the embodiments disclosed herein may be substituted with different elements configured to perform the same or similar functions as those disclosed herein. Additionally, any of the embodiments disclosed herein may include such structural elements as necessary to accomplish the intended functions of the embodiments. Accordingly, any of the embodiments disclosed herein may further include structural elements such as ribs, ridges, grooves, flanges, etc., as needed to accomplish the intended functions.

In any of the embodiments disclosed herein, the properties of the clip arm 665 may be configured to control the force at which the detent 666, 646 disengages. As described above, this disengagement may be due to pressure within the syringe body 610. Thus, the properties of the clip arm 665, the slidable prong 680, and the seal 642 may be configured to control the pressure at which the inflation device 600 shifts configurations. The clip arm 665 may be a cantilevered component coupled to the locking sleeve 660 only at its base. Thus, the length, the thickness, and the material properties of the clip arm 665 may each impact the force required to disengage the detent 666, 646. In some embodiments, this may be adjustable by a user. For example, the clip arm 665 may be configured with a ring disposed around a circumference of the locking sleeve 660, the ring configured to be disposed about the clip arm 665. Rotating the ring may be configured to adjust compression of the clip arm 665 against the tip portion 686 of the prong arm 688 to thereby modulate the frictional resistance to proximal movement of the tip portion 686. Rotating the ring one direction may increase (compression and rotating the ring the other direction may decrease compression. Thus, the force required for slidable prong 680 to push the tip clip 666 out of engagement with the recess portion 646 may be adjustable by a user. The ring may adjust compression by having a variable inner diameter, for instance.

FIG. 32 is a cross-sectional view of the inflation device of FIG. 30, taken through plane 32-32. The handle 620, shaft 625, syringe body 610, outer plunger 630, intermediate plunger 640, inner plunger 650, and locking sleeve 660 are shown in this figure. The biasing elements 668 and locking rails 670 are also shown, along with the locking rail angled surfaces 675, the intermediate plunger angled surfaces 645, the locking sleeve threads 672, and the cap threads 619. Further, the intermediate plunger cap 649 as well as the shaft shoulder 629 are illustrated. This cross-sectional view illustrates how the shaft shoulder 629 and intermediate plunger cap 649 may interact to pull the intermediate plunger 640 proximally when the handle 620 is displaced proximally and the shaft shoulder 629 is in contact with the intermediate plunger cap 649.

FIGS. 33A-38 illustrate an alternative embodiment of the inflation device 600 with an alternative intermediate plunger 640' and a valve 690. The only difference between the intermediate plunger 640' and the intermediate plunger 640 is that the distal plunger face 640a includes the groove 640b recessed in the distal end of the intermediate plunger 640'.

As illustrated in FIG. 33A-33D, the valve 690 may comprise the perforated disk 691 and the seal 692. The proximal face of the perforated disk 691 may comprise the protruding ring 694 configured to mate with the groove 640b. The portion of the proximal face of the perforated disk 691 radially extending beyond the protruding ring 694 may be configured to mate with the distal plunger face 640a. The seal 692 may comprise a stem 694 configured for insertion in a mounting hole 695 of the perforated disk 691. The stem 694 may be comprised of an elastomeric material. The stem 694 may be integrally molded with the rest of the seal 692. The stem 694 may comprise a bulge region configured and located to retain the seal 692 flush against the proximal face of the perforated disk 691. The disk 691 may be configured to be rigid and the seal 692 may be configured to be flexible.

Figure 36:
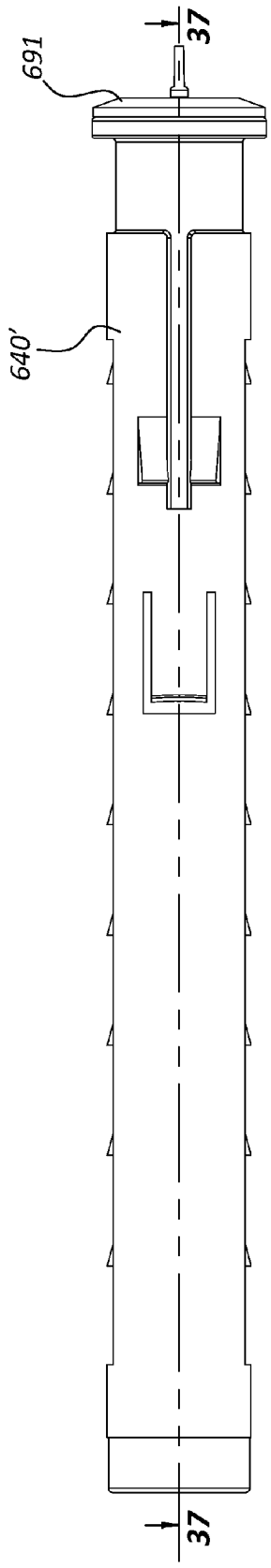
FIG. 36 is a top view of the assembled intermediate plunger and valve illustrated in FIG. 33B and FIG. 33D.
Figure 37:
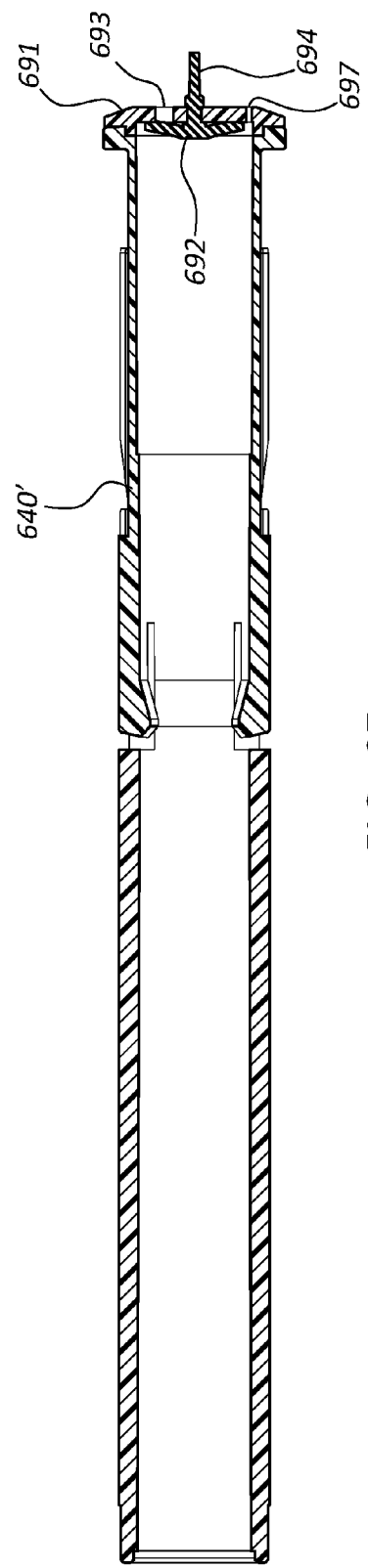
FIG. 37 is a cross-sectional view of the assembly of FIG. 36 taken through plane 37-37.

FIG. 34 illustrates a side view of the intermediate plunger 640'. FIG. 35 illustrates a cross-sectional view of the same along the plane 35-35. FIG. 36 illustrates a top view of the intermediate plunger 640'. FIG. 37 illustrates a cross-sectional view of the same along the plane 37-37. Referring to FIGS. 35 and 37, the seal 692 may have a diameter large enough to cover the inflow holes 693 formed in the perforated disk 691. The perforated disk 691 may comprise a weep hole 697 formed therein. The weep hole 697 may have a diameter of a few hundredths of an inch, such as, for example, 0.025th of an inch. The seal 692 may not have a diameter wide enough to cover the weep hole 697.

Figure 38:
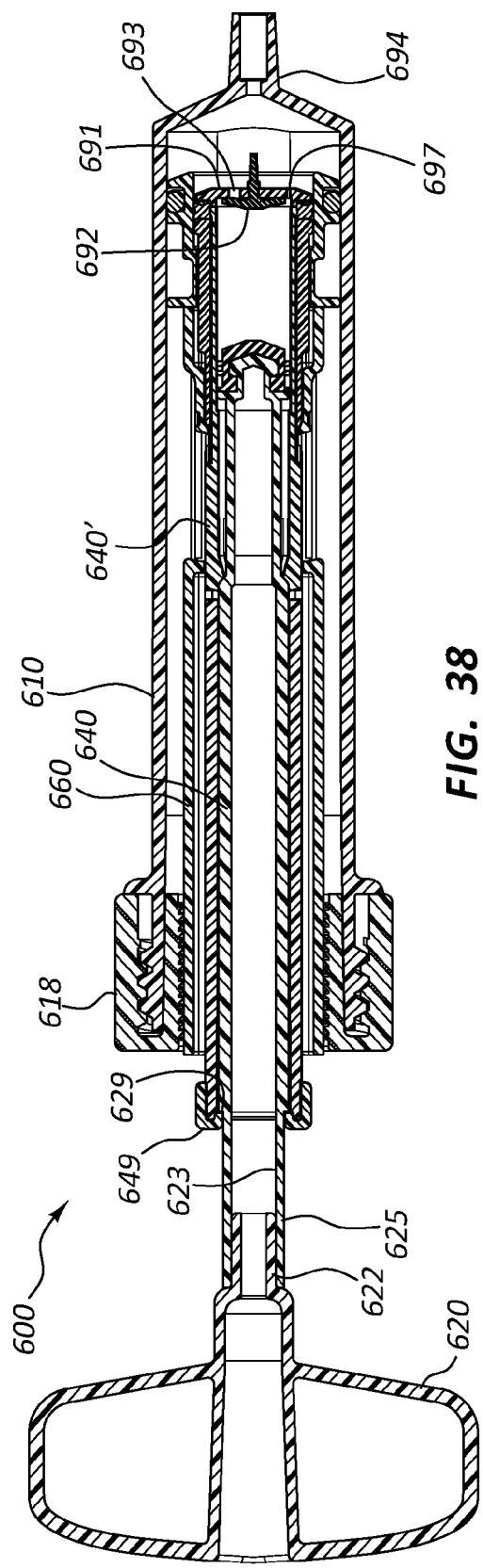
FIG. 38 is a cross-section view of an inflation device similar to FIG. 31, but with the intermediate plunger and the valve of FIG. 33B and FIG. 33D.

FIG. 38 illustrates a cross-section view of the inflation device 600 similar to FIG. 31, but with the intermediate plunger 640' and the valve 690 in place (and without the gauge mounting bracket 617 visible).

Operation of the valve 690 will now be described. The valve 690 may be configured to prevent too rapid of pressurizing of medical devices, such as balloons. For example, the valve 690 may be configured to prevent the bursting of balloons during inflation, but still allow rapid deflation. During the pressurizing of the interior of the syringe body 610 by distal movement of the outer plunger 630 and/or the intermediate plunger 640', the pressure on either side of the valve 690 may tend to stay equal by virtue of the weep hole 697. As the inflation device 600 shifts to the locked configuration, there may be a tendency for the inner plunger 650 to rapidly move distally and thereby rapidly increase the pressure within the syringe body 610 and any attached medical device. With the valve 690 in place, if the inner plunger 650 rapidly moves distally, pressure may temporarily increase on the proximal side of the valve 690 and then slowly bleed into the remainder of the syringe body 610 through the weep hole 697. In that manner, an attached medical device may be rapidly inflated, but then slowly highly pressurized.

In contrast, the valve 690 may allow for rapid depressurization and deflation. With the inflation device 600 in the locked configuration, the inner plunger 650 may be rapidly retracted (pulled back in the proximal direction), but not retracted so far as to unlock the inflation device. The rapid increase in volume on the proximal side of the valve 690 will cause a pressure drop on that side. High pressure fluid on the distal side of the valve 690 will push against the seal 692 through the inflow holes 693. This may stretch stem 694 and/or deform the seal 692 sufficient to allow high pressure fluid flow through the inflow holes 693 (i.e., open the valve 690). At the same time, at a lower flow rate, high pressure fluid would flow through the weep hole 697. In this manner, a medical device may be rapidly depressurized. Of course, the medical device may also be slowly depressurized by slowing retracting the inner plunger 650 and relying solely upon fluid transfer through the weep hole 697. The medical device may then be slowly or rapidly deflated by retracting the handle 620 with the inflation device 600 in the unlocked configuration Additionally, upon the switch of the inflation device 600 into the unlocked configuration, the pressure would drop on the distal side of the valve 690 and the pressure on the proximal side of the valve 690 would tend to keep seal 692 in place, blocking fluid flow through the inflow holes 693. The pressure on the proximal side of the valve 690 would tend to equalize with the lower pressure on the distal side.

During rapid inflation of a medical device and prior to the inflation device 600 switching to the locked configuration, enough pressure may build up on the distal side of the valve 690 to partially or fully open the valve 690. However, as soon as pressures equalized and/or pressure increased on the proximal side of the valve 690 (such as by the switch to the locked configuration and distal movement of the inner plunger 650 continuing while the outer plunger 630 and the intermediate plunger 640' have substantially stopped moving), then the valve 690 would close.

The valve 690 may be configured to work with the intermediate plunger 140 and the intermediate plunger 240 and vice versa. Additionally, the valve 690 may be configured to work with any number of inflation devices.

Without further elaboration, it is believed that one skilled in the art can use the preceding description to utilize the present disclosure to its fullest extent. The examples and embodiments disclosed herein are to be construed as merely illustrative and exemplary, and not a limitation of the scope of the present disclosure in any way. It will be apparent to those having skill in the art that changes may be made to the details of the above-described embodiments without departing from the underlying principles of the disclosure herein. It is intended that the scope of the invention be defined by the claims appended hereto and their equivalents.

The invention claimed is:

1. An inflation device configured to displace fluid within a medical device, the inflation device comprising:
   a body member defining a reservoir;
   a first plunger displaceable within the body member, the first plunger configured to displace fluid within the reservoir;
   a second plunger displaceable within the body member, the second plunger configured to displace fluid within the reservoir;
   a handle operably coupled to the first and second plungers; and
   a thread rail configured to selectively couple the first plunger to the body member, the thread rail configured such that interaction between the thread rail and the first plunger forces the thread rail radially outward when the first plunger is in a locked configuration;
   wherein the inflation device is configured to transition from an unlocked configuration to the locked configuration as the handle is displaced to eject fluid from the reservoir;
   wherein the first and second plungers are displaceable with respect to the body member when the inflation device is in the unlocked configuration; and
   wherein the second plunger, but not the first plunger, is displaceable with respect to the body member when the inflation device is in the locked configuration.

2. The inflation device of claim 1, wherein an effective surface area, acting on the reservoir, of the first plunger is larger than an effective surface area, acting on the reservoir, of the second plunger.

3. The inflation device of claim 1, wherein the first plunger is coupled to the body member when the inflation device is in the locked configuration.

4. The inflation device of claim 3, wherein the first plunger comprises an outer plunger and an intermediate plunger and wherein the outer plunger is releasably coupled to the intermediate plunger.

5. The inflation device of claim 4, wherein the intermediate plunger is configured to release from the outer plunger when forces acting on the outer plunger are sufficient to overcome forces acting on a detent operably coupling the intermediate plunger to the outer plunger.

6. The inflation device of claim 4, wherein the intermediate plunger is configured to release from the outer plunger when the pressure inside the reservoir exceeds a given pressure.

7. The inflation device of claim 3, wherein the reservoir comprises a first portion and a second portion, and wherein the first plunger is selectively displaceable within the first portion and the second plunger is selectively displaceable within the second portion.

8. The inflation device of claim 1, further comprising a valve operably coupled to the first plunger and configured to retard rapid displacement of fluid within the reservoir by the second plunger.

9. An inflation device comprising:
a syringe body defining a reservoir;
a first plunger disposed within the syringe body, the first plunger comprising an outer plunger and an intermediate plunger that are releasably coupled to each other;
a second plunger disposed within the first plunger; and
a handle operably coupled to the first and second plungers, the handle configured to displace the first and second plungers with respect to the syringe body; and
a locking sleeve disposed around the intermediate plunger, the locking sleeve comprising a guide groove that interacts with the intermediate plunger to resist rotation of the intermediate plunger relative to the locking sleeve.

10. The inflation device of claim 9, wherein the locking sleeve is coupled to the outer plunger and the locking sleeve is releasably coupled to the intermediate plunger.

11. The inflation device of claim 10, wherein displacement of the locking sleeve with respect to the intermediate plunger is configured to selectively couple the locking sleeve and the intermediate plunger to the syringe body.

12. The inflation device of claim 10, wherein the second plunger is releasably coupled to the first plunger.

13. The inflation device of claim 10, wherein the locking sleeve is configured to automatically decouple from the intermediate plunger when pressure within the reservoir reaches a given pressure.

14. The inflation device of claim 9, further comprising a valve operably coupled to the intermediate plunger.

15. The inflation device of claim 9, further comprising one or more thread rails, the thread rails configured to releasably couple the first plunger to the syringe body.

16. An inflation device comprising:
a syringe body defining a reservoir;
a first plunger disposed within the syringe body;
a valve that remains attached to the first plunger adjacent a distal end of the first plunger throughout operation of the inflation device, wherein the valve is configured to both retard rapid distal displacement of fluid across the valve as the first plunger is advanced distally within the syringe body and to allow rapid proximal displacement of fluid across the valve as the plunger is retracted proximally within the syringe body; and
a handle operably coupled to the first plunger, the handle configured to displace the first plunger with respect to the syringe body.

17. The inflation device of claim 16, wherein the valve comprises a seal configured to only allow fluid flow in one direction.

18. The inflation device of claim 17, wherein the valve further comprises a weep hole located and configured to allow continuous fluid flow independent of the seal.

19. The inflation device of claim 17, wherein the valve further comprises a perforated disk with inflow holes formed therein, wherein the seal is configured to cover the inflow holes unless the seal is deformed or displaced by sufficiently pressurized fluid flow in the one direction.

20. A method of displacing fluid within an inflation device, the method comprising:
displacing a handle of the inflation device in a distal direction from a first position to a second position such that a first plunger, coupled to the handle, displaces fluid within a reservoir of the inflation device;
locking the first plunger to a body member of the inflation device, by displacing a locking component radially outward from the first plunger, to prevent proximal displacement of the first plunger with respect to the body member;
displacing the handle of the inflation device in a distal direction from the second position a third position such that a second plunger, coupled to the handle, displaces fluid within the reservoir while the first plunger is locked with respect to the body member;
wherein a maximum force needed to displace the handle from the second position to the third position is smaller in magnitude than a maximum force needed to displace the handle from the first position to the second position.

21. The method of claim 20, wherein:
the first plunger is locked to the body member of the inflation device after the handle has been displaced from the first position to the second position; and
displacing the handle of the inflation device in the distal direction from the second position to the third position fully evacuates the reservoir.

* * * * *

UNITED STATES PATENT AND TRADEMARK OFFICE
CERTIFICATE OF CORRECTION

| | | |
|---|---|---|
| PATENT NO. | : 9,452,279 B2 | Page 1 of 1 |
| APPLICATION NO. | : 14/021054 | |
| DATED | : September 27, 2016 | |
| INVENTOR(S) | : Brian Stevens et al. | |

It is certified that error appears in the above-identified patent and that said Letters Patent is hereby corrected as shown below:

In the claims

Column 28, Line 34 reads, ". . . the second position a third position . . ." which should read ". . . the second position to a third position . . ."

Signed and Sealed this
Twentieth Day of December, 2016

Michelle K. Lee
*Director of the United States Patent and Trademark Office*